US011471419B2

(12) United States Patent
Kim et al.

(10) Patent No.: US 11,471,419 B2
(45) Date of Patent: *Oct. 18, 2022

(54) CAPSULES WITH INTRACAPSULAR MICROSPHERES FOR IMPROVED SURVIVAL AND FUNCTION OF ENCAPSULATED CELLS

(71) Applicant: The Board of Trustees of the University of Illinois, Urbana, IL (US)

(72) Inventors: Kyekyoon Kim, Champaign, IL (US); Hyungsoo Choi, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/721,045

(22) Filed: Sep. 29, 2017

(65) Prior Publication Data
US 2018/0092855 A1    Apr. 5, 2018

Related U.S. Application Data

(60) Provisional application No. 62/402,133, filed on Sep. 30, 2016.

(51) Int. Cl.
*A61K 9/50* (2006.01)
*A61K 9/48* (2006.01)
(Continued)

(52) U.S. Cl.
CPC .......... *A61K 9/5036* (2013.01); *A61K 9/4866* (2013.01); *A61K 9/5089* (2013.01);
(Continued)

(58) Field of Classification Search
None
See application file for complete search history.

(56) References Cited

U.S. PATENT DOCUMENTS 5,578,314 A * 11/1996 Cochrum ............. A61K 9/0024
424/424
5,919,446 A     7/1999 Pusey
(Continued)

FOREIGN PATENT DOCUMENTS

WO    WO 2008/063465      *  5/2008
WO    WO 2008/063465 A2      5/2008
(Continued)

OTHER PUBLICATIONS

Qi et al., Colloids and Surfaces B: Biointerfaces 112: 492-498 (2013).*
(Continued)

*Primary Examiner* — Erin M. Bowers
(74) *Attorney, Agent, or Firm* — Leydig, Voit & Mayer, Ltd.

(57) ABSTRACT

Provided is a microcapsule for increasing the survival and/or function of a cell, such as an islet cell, microcapsule can include an outer shell comprising a first polymer; an interior core comprising: at least one live cell; a second polymer; and at least one microsphere comprising a third polymer and a compound capable of improving survival of the at least one cell. The improved survival and/or function of the at least one live cell in the microcapsule is compared to a live cell in a microcapsule in the absence of the compound capable of improving survival of the at least one cell. The first and second polymer may include alginate and the third polymer (used for the microsphere) may comprise PLGA. The compound may include a GLP-1 receptor agonist. Also provided are methods for producing such microcapsules; insulin delivery systems using the microcapsules, and methods to treat disease, such as diabetes, using the microcapsules.

6 Claims, 5 Drawing Sheets

(51) Int. Cl.
A61P 3/10 (2006.01)
A61K 38/22 (2006.01)
A61K 35/39 (2015.01)

(52) U.S. Cl.
CPC .......... *A61K 35/39* (2013.01); *A61K 38/2278* (2013.01); *A61P 3/10* (2018.01)

(56) References Cited

U.S. PATENT DOCUMENTS

| | | | |
|---|---|---|---|
| 6,669,961 | B2 | 12/2003 | Kim et al. |
| 7,309,500 | B2 | 12/2007 | Kim et al. |
| 7,368,130 | B2 | 5/2008 | Kim et al. |
| 8,293,271 | B2 | 10/2012 | Kim et al. |
| 8,409,621 | B2 | 4/2013 | Kim et al. |
| 8,663,511 | B2 | 3/2014 | Kim et al. |
| 2007/0190036 | A1 | 8/2007 | Kizilel et al. |
| 2008/0050417 | A1 | 2/2008 | Dufrane et al. |
| 2008/0175915 | A1 | 7/2008 | Kim et al. |
| 2009/0269313 | A1 | 10/2009 | Nadler |
| 2012/0231443 | A1 | 9/2012 | He et al. |
| 2014/0127290 | A1 | 5/2014 | He et al. |
| 2014/0212484 | A1 | 7/2014 | Krotz et al. |
| 2018/0070586 | A1 | 3/2018 | Kim et al. |
| 2021/0322326 | A1 | 10/2021 | Choi et al. |

FOREIGN PATENT DOCUMENTS

| | | |
|---|---|---|
| WO | WO 2012/101167 A1 | 8/2012 |
| WO | WO 2013/089925 A1 | 6/2013 |

OTHER PUBLICATIONS

Padmasekar et al., Endocrinology 154: 1424-1433 (2013).*

Whelehan et al., J. Microencapsulation 28(8): 669-688 (2011).*

Anderson et al. (1997) "Biodegradation and biocompatibility of PLA and PLGA microspheres," Advanced Drug Delivery Reviews. 28(1):5-24.

Bashan (1998) "Inoculants of Plant Growth-Promoting Bacteria for Use in Agriculture," Biotechnol. Adv. 16:729-770.

Berkland et al. (2001) "Fabrication of PLG microspheres with precisely controlled and monodisperse size distributions," Journal of Controlled Release. 73(1):59-74.

Berkland et al. (2002) "Precise control of PLG microsphere size provides enhanced control of drug release rate," Journal of Controlled Release. 82(1):137-47.

Bloemberg et al. (2000) "Simultaneous imaging of Pseudomonas fluorescens WCS365 populations expressing three different autofluorescent proteins in the rhizosphere: new perspectives for studying microbial communities," Mol. Plant Microbe Interact. 13(11):1170-6.

Bonaterra et al. (2005) "Osmotically induced trehalose and glycine betaine accumulation improves tolerance to desiccation, survival and efficacy of the postharvest biocontrol agent Pantoea agglomerans EPS125," FEMS Microbiology Letters. 250:1-8.

Bonaterra et al. (2007) "Increasing survival and efficacy of a bacterial biocontrol agent of fire blight of rosaceous plants by means of osmoadaptation," FEMS Microbiol. Ecol. 61:185-195.

Bonn et al. (2000) "Distribution and economic importance of fire blight," In; Fire blight the disease and its causative agent, Erwinia amylovora. Ed: Vanneste. CABI Publishing. Wallingford, UK. pp. 37-54.

Brandhorst et al. (1999) "Significant progress in porcine islet mass isolation utilizing liberase HI for enzymatic low-temperature pancreas digestion," Transplantation. 68(3):355-61.

Buss et al. (2012) "Exenatide Pretreatment Improved Graft Function in Nonhuman Primate Islet Recipients Compared to Treatment after Transplant Only," Journal of Transplantation. 2012:382518. pp. 1-10.

Cabrefiga et al. (Jul. 5, 2014) "Improvement of a dry formulation of Pseudomonas fluorescens EPS62e for fire blight disease biocontrol by combination of culture osmoadaptation with a freeze-drying lyoprotectant," Journal of Applied Microbiology. 117:1122-1131.

Carter et al. (2009) "A practical guide to rodent islet isolation and assessment," Biological Procedures Online. 11:3-31.

Champagne et al. (1996) "Effect of polymers and storage temperature on the stability of freeze-dried lactic acid bacteria," Food Research International. 29:555-562.

Cheng et al. (2011) "Modeling of small-molecule release from crosslinked hydrogel microspheres: effect of crosslinking and enzymatic degradation of hydrogel matrix," International Journal of Pharmaceutics. 403(1-2):90-5.

Costa et al. (2000) "Effect of protective agents, rehydration media and initial cell concentration on viability of Pantoea agglomerans strain CPA-2 subjected to freeze-drying," J. Appl. Microbiol. 89:793-800.

Csonka et al. (1991) "Prokaryotic osmoregulation: genetics and physiology," Annu. Rev. Microbiol. 45:569-606.

De Groot et al. (2004) "Causes of limited survival of microencapsulated pancreatic islet grafts," The Journal of Surgical Research. 121(1):141-50.

Denning (1794) "On the decay of apple trees," Trans. Soc. Prom. Agric. Arts Manuf. Trans. 2:219-222.

Dianawati et al. (Jan. 24, 2013) "Survival of Bifidobacterium longum 1941 microencapsulated with proteins and sugars after freezing and freeze drying," Food Research International. 51:503-509.

Epton et al. (1994) "Biological control of Erwinia amylovora with Erwinia herbicola," In; Ecology of Plant Pathogens. Eds: Blakeman et al. CAB International. Wallingford, UK. pp. 335-352.

Gaba et al. (2012) "Pancreatic islet cell transplantation: an update for interventional radiologists," Journal of Cascular and Interventional Radiology. 23(5):583-94; quiz 594.

Galinski (1995) "Osmoadaptation in bacteria," Adv. Microb. Physiol. 37:272-328.

Geng et al. (2008) "Formulating erythropoietin-loaded sustained-release PLGA microspheres without protein aggregation," Journal of Controlled Release. 130(3):259-65.

Hamoudi et al. (2007) "Effect of protective agents on the viability of geotrichum candidum during freeze-drying and storage," Journal of Food Science. 72:M45-49.

Holdcraft et al. (Apr. 29, 2013) "Enhancement of In Vitro and In Vivo Function of Agarose-EncapsualtedPorcine Islets by Changes in the Islet Microenvironment," Cell Transplant. 23(8):929-44.

Huq et al. (Feb. 24, 2012) "Encapsulation of Probiotic Bacteria in Biopolymeric System," Crit. Rev. Food Sci. Nutr. 53:909-916.

Ishimaru et al. (1988) "Multiple Antibiotic Production by Erwinia-Herbicola," Phytopathology. 78:746-750.

Jeong et al. (2012) "Functional enhancement of beta cells in transplanted pancreatic islets by secretion signal peptide-linked exendin-4 gene transduction," Journal of Controlled Release. 159(3):368-75.

Jock et al. (Apr. 6, 2013) "Molecular analyses of Erwinia amylovora strains isolated in Russia, Poland, Slovenia and Austria describing further spread of fire blight in Europe," Microbiological Research. 168:447-454.

Johnson (1940) "The maintenance of high atmospheric humidities for entomological work with glycerol-water mixtures," Ann. Appl. Biol. 27:295-297.

Johnson et al. (1993) "Effect of Antagonistic Bacteria on Establishment of Honey Bee-Dispersed Erwinia-Amylovora in Pear Blossoms and on Fire Blight Control," Phytopathology. 83:995-1002.

Kearney et al. (1990) "Enhancing the viability of Lactobacillus-Plantarum inoculum by immobilizing the cells in calcium-alginate beads incorporating cryoprotectants," Appl. Environ. Microb. 56:3112-3116.

Kim et al. (2007) "Evaluation of semi-interpenetrating polymer networks composed of chitosan and poloxamer for wound dressing application," Int. J. Pharm. 341:35-43.

Kim et al. (2012) "Controlled Release of Pantoea agglomerans E325 for Biocontrol of fire blight disease of apple," Journal of Controlled Release 161:109-115.

(56) References Cited

OTHER PUBLICATIONS

Leben (1988) "Relative-Humidity and the Survival of Epiphytic Bacteria with Buds and Leaves of Cucumber Plants," Phytopathology. 78:179-185.
Lim et al. (1980) "Microencapsulated islets as bioartificial endocrine pancreas," Science. 210(4472):908-10.
Lindow (1984) "Integrated control and role of antibiosis in biological control of fire blight and frost injury," In; Biological Control on the Phylloplane. Eds.: Windels et al. The American Phytopathological Society. St. Paul, MN. pp. 83-115.
Liu et al. (2010) "Preparation, characterization, and pharmacodynamics of exenatide-loaded poly(DL-lactic-co-glycolic acid) microspheres," Chemical & Pharmaceutical Bulletin. 58(11):1474-9.
Ma (Sep. 10, 2014) "Microencapsulation of protein drugs for drug delivery: strategy, preparation, and applications," Journal of Controlled Release. 193:324-40.
McManus et al. (1994) "Epidemiology and genetic analysis of streptomycin resistant Erwinia amylovora from Michigan and evaluation of oxytetracycline for control," Phytopathology. 84:627-633.
McManus et al. (2002) "Antibiotic use in plant agriculture," Annual Review of Phytopathology. 40:443-65.
Meinel et al. (2001) "Stabilizing insulin-like growth factor-I in poly(D,L-lactide-co-glycolide) microspheres," Journal of Controlled Release. 70(1-2):193-202.
Mineo et al. (2009) "Point: steady progress and current challenges in clinical islet transplantation," Diabetes Care. 32(8):1563-9.
Moller et al. (1981) "The Scenario of Fire Blight and Streptomycin Resistance," Plant Disease. 65:563-568.
Montesinos (2003) "Development, registration and commercialization of microbial pesticides for plant protection," International Microbiology. 6:245-252.
Padmasekar et al. (Mar. 7, 2013) "Exendin-4 protects hypoxic islets from oxidative stress and improves islet transplantation outcome," Endocrinology. 154(4):1424-33.
Paul et al. (1993) "Survival of Alginate-Entrapped Cells of Azospirillum lipoferum During Dehydration and Storage in Relation to Water Properties," Appl. Microbiol. Biotechnol. 40:34-39.
Paulin (1996) "Control of fireblight in European pome fruits," Outlook on Agriculture. 25:49-55.
Pileggi et al. (2001) "Factors influencing Islet of Langerhans graft function and monitoring," Clinica Chimica Acta. 310(1):3-16.
Potter et al. (2010) "Islet amyloid deposition limits the viability of human islet grafts but not porcine islet grafts," Proc. Natl. Acad. Sci. USA. 107(9):4305-10.
Prentki et al. (2006) "Islet beta cell failure in type 2 diabetes," The Journal of Clinical Investigation. 116(7):1802-12.
Pusey (1997) "Crab apple blossoms as a model for research on biological control of fire blight," Phytopathology. 87:1096-1102.
Pusey et al. (2004) "Temperature and pomaceous flower age related to colonization by Erwinia amylovora and antagonists," Phytopathology. 94:901-911.
Pusey et al. (2008) "Antibiosis and acidification by Pantoea agglomerans strain E325 may contribute to suppression of Erwinia amylovora," Phytopathology. 98:S128-S128.
Pusey et al. (2011) "Antibiosis by Pantoea agglomerans biocontrol strain E325 against Erwinia amylovora on apple flower stigmas," Phytopathology. 101:S146-S147.
Qi (Jan. 30, 2014) "Transplantation of Encapsulated Pancreatic Islets as a Treatment for Patients with Type 1 Diabetes Mellitus," Advances in Medicine. 2014:429710. pp. 1-15.
Qi et al. (2008) "Encapsulation of human islets in novel inhomogeneous alginate-$Ca^{2+}$/$Ba^{2+}$ microbeads: in vitro and in vivo function," Artificial Cells, Blood Substitutes, and Immobilization Biotechnology. 36(5):403-20.
Qi et al. (Sep. 7, 2013) "Preparation of uniform-sized exenatide-loaded PLGA microspheres as long-effective release system with high encapsulation efficiency and bio-stability," Colloids and Surfaces B, Biointerfaces. 112:492-8.
Qutachi et al. (Aug. 23, 2014) "Injectable and porous PLGA microspheres that form highly porous scaffolds at body temperature," Acta Biomater. 10(12):5090-5098.
Ramazani et al. (Jan. 12, 2016) "Strategies for encapsulation of small hydrophilic and amphiphilic drugs in PLGA microspheres: State-of-the-art and challenges," International Journal of Pharmaceutics. 499(1-2):358-67.
Ricordi et al. (1986) "A method for the mass isolation of islets from the adult pig pancreas," Diabetes. 35(6):649-53.
Ricordi et al. (1990) "Islet isolation assessment in man and large animals," Acta Diabetologica Latina. 27(3):185-95.
Sakata et al. (2012) "Encapsulated islets transplantation: Past, present and future," World Journal of Gastrointestinal Pathophysiology. 3(1):19-26.
Sato et al. (2011) "Cellular hypoxia of pancreatic beta-cells due to high levels of oxygen consumption for insulin secretion in vitro," The Journal of Biological Chemistry. 286(14):12524-32.
Semyonov et al. (2010) "Microencapsulation of Lactobacillus paracaseiby spray freeze drying", Food Research International. 43(1):193-202.
Shimoda et al. (2012) "Improvement of porcine islet isolation by inhibition of trypsin activity during pancreas preservation and digestion using alpha1-antitrypsin," Cell Transplantation. 21(2-3):465-71.
Stockwell et al. (2006) "Colonization of flowers by Pseudomonas fluorescens A506 formulated in a biopolymer gel," Acta Hort. 704:293-300.
Strand et al. (2003) "Visualization of alginate-poly-L-lysine-alginate microcapsules by confocal laser scanning microscopy," Biotechnology and Bioengineering. 82(4):386-94.
Strasser et al. (2009) "Influence of lyophilization, fluidized bed drying, addition of protectants, and storage on the viability of lactic acid bacteria," J Appl. Microbiol. 107:167-177.
Thomson (1986) "The Role of the Stigma in Fire Blight Infections," Phytopathology. 76:476-482.
Thomson et al. (1975) "Occurrence of fire blight of pear in relation to weather and epiphytic populations of Erwinia amylovora," Phytopathology. 65:576-579.
Wilson et al. (1992) "Interactions between Erwinia-Herbicola and E-Amylovora on the Stigma of Hawthorn Blossoms," Phytopathology. 82:914-918.
Wynyard et al. (May 7, 2014) "Microbiological safety of the first clinical pig islet xenotransplantation trial in New Zealand," Xenotransplantation. 21(4):309-23.
Yang et al. (Apr. 6, 2015) "Current status of encapsulated islet transplantation," Journal of Diabetes and its Complications. 29(5):737-43.
Zhu et al. (Mar. 24, 2014) "Pig-islet xenotransplantation: recent progress and current perspectives," Frontiers in Surgery. 1:7. pp. 1-8.
Zhu et al. (May 11, 2015) "Comparative studies on exenatide-loaded poly (D,L-lactic-co-glycolic acid) microparticles prepared by a novel ultra-fine particle processing system and spray drying," Colloids and Surfaces B, Biointerfaces. 132:103-10.
U.S. Appl. No. 15/680,590, filed Aug. 18, 2017.

\* cited by examiner

CAPSULES WITH INTRACAPSULAR MICROSPHERES FOR IMPROVED SURVIVAL AND FUNCTION OF ENCAPSULATED CELLS

CROSS-REFERENCE TO RELATED APPLICATIONS

The present application is a U.S. utility patent application claiming priority to pending U.S. Ser. No. 62/402,133, entitled "Capsules with Intracapsular Microspheres for Improved Survival and Function of Encapsulated Cells," filed Sep. 30, 2016, which is incorporated herein by reference for all that is taught and disclosed.

BACKGROUND OF INVENTION

The most common form of therapy for type 1 diabetes mellitus (T1 DM) involves lifelong administration of exogenous insulin and frequent/continuous monitoring of blood glucose levels, providing a suboptimal glycemic control at best. Tighter glucose control can be attained through whole pancreas transplantation that involves complicated surgical procedures, high morbidity, lifelong immunosuppressive medication and consequential complications. Allogeneic islet transplantation has emerged as a promising alternative to these treatments. This minimally invasive procedure results in no or fewer complications and thus may be utilized for a wider range of recipients; however, it is limited by the scarcity of human pancreas donors and the graft failure within a relatively short period of time compared with whole pancreas transplantation (Gaba et al., 2012; Qi, 2014). In this context, transplantation of encapsulated porcine islets is an attractive strategy due to donor abundance and accessibility, allowing long-term immunoisolation (Lim and Sun, 1980). Porcine pancreas is considered as a prospective source of islet xenografts due to similarities in pig physiology to humans, structural similarity between human and porcine insulin, resistance to recurrent autoimmunity, and feasibility for genetic immunomodulation (Potter et al., 2010; Wynyard et al., 2014; Zhu et al., 2014).

Many studies have shown encouraging results in reducing xenogeneic rejection and prolonging graft survival time. Nevertheless, several challenges still remain to be overcome before their clinical applications, such as high-throughput encapsulation, and prevention of hypoxia and improvement of islet function (Mineo et al., 2009; Sakata et al., 2012; Yang and Yoon, 2015). Pancreatic β-cells consume large amounts of oxygen during glucose-stimulated insulin secretion (GSIS) (Sato et al., 2011). Islets lack vasculature in the early post-transplantation period, resulting in a hypoxic environment to compromise graft success and function (Pileggi et al., 2001). It was reported that exendin-4, a glucagon-like peptide-1 analog, was able to improve the survival of transplanted islets in mice by reducing oxidative stress in β-cells and to enhance glucose-stimulated insulin secretion (GSIS) (Padmasekar et al., 2013). In accordance with this, in a mouse model, the islet mass required to achieve normoglycemia was reduced by transplanting exendin-4 gene transduced islets via the secretion of exendin-4 at the transplantation site, attenuating the adverse effects of systemic exendin-4 (Jeong et al., 2012).

However, providing systemic exenatide to a patient to support recently transplanted islet cells has adverse effects. A need remains for a system for providing localized, sustained on-site release of exenatide to encapsulated islets to improve viability and insulin-secretion function. Accordingly, it would be desirable to obtain such an encapsulated cell demonstrating improved survival and function of the cell, useful for methods of treating disease or for providing an insulin delivery system.

SUMMARY OF THE INVENTION

The present invention arises from the investigation of the effect of locally released exenatide, a synthetic version of exendin-4, on the survival and function of porcine islets encapsulated in alginate microcapsules in vitro for 21 days, employing exenatide-loaded poly(lactic-co-glycolic acid) (PLGA) microspheres (MSs) as intracapsular drug depots. PLGA has been widely used as a medical-grade biodegradable polymer in surgical sutures, bone plates, orthopedic implants and drug delivery system. The studies showed sustained on-site release of exenatide on the survival and function of encapsulated islets, employing exenatide-loaded PLGA MSs. The PLGA MSs were monodisperse, exhibiting sustained exenatide release during the 21-day period with minimal initial burst. The porcine islets co-encapsulated with the exenatide-loaded PLGA MSs in alginate microcapsules showed improved viability and GSIS function. This implies that the microsphere-mediated on-site release of exenatide could provide potential benefits to islet transplantation, especially during the early post-transplantation period lacking vasculature, while mitigating the adverse effects of systemic exenatide.

In one embodiment, the present invention includes a microcapsule for improved survival and/or function of encapsulated cells. The microcapsule can include an outer shell comprising a first polymer; an interior core comprising: at least one live cell; a second polymer; and at least one microsphere comprising a third polymer and a compound capable of improving survival of the at least one cell. The improved survival and/or function of the at least one live cell in the microcapsule is compared to a live cell in a microcapsule in the absence of the compound capable of improving survival of the at least one cell.

In the microcapsule, the first and second polymer may be independently selected from the group consisting of alginate, ethyl cellulose, hyaluronic acid, chitosan, agarose, hydroxypropyl methylcellulose, polyvinyl alcohol copolymer, polyethylene glycol, and gelatin. The live cell may be selected from a human live cell or a non-human eukaryotic live cell. In some embodiments, the live cell can include a pancreatic islet cell, a primary liver cell (hepatocyte), a mesenchymal stem cell, a neuron, or a fibroblast. In one embodiment, the live cell is a porcine pancreatic islet cell.

The microcapsule includes microspheres which are capable of slowly releasing the compound into the interior core of the microcapsule. The microsphere may comprise a third polymer selected from one or more of poly(glycolic acid), poly(lactic acid), poly(lactic-co-glycolic acid) (PLGA) and their copolymers, poly(ester amides), poly(ε-caprolactones) (PCL) and their copolymers, polyurethanes, polymethacrylates, poly(anhydrides), poly(phosphoesters) and their copolymers. The microsphere may be a monodispersed emulsion comprising an aqueous polyvinyl alcohol solution, compound capable of improving the survival of the at least one cell mixture, and a PLGA solution in an organic solvent. In some embodiments, the organic solvent is dichloromethane, the aqueous polyvinyl alcohol is between 0.1 and 10%, the PLGA solution is between 2-10% (w/v), and the compound is between 5% load and 10% load, and the microcapsules are hardened microcapsules.

In some embodiments, the compound capable of improving survival of the at least one cell comprises one or more of a glucagon-like peptide-1 (GLP-1) receptor agonist, an anti-inflammatory drug, a pro-angiogenic drug, a chelating agent, and a corticosteroid. Where the compound is a GLP-1 receptor agonist, the agonist may include exenatide, exendin-4, truncated exendin-4, esterified exendin-4, N-alkyl exendin-4, PEG-modified exendin-4, liraglutide, lixisenatide, dulaglutide, taspoglutide, and semaglutide. Where the compound is a corticosteroid, the corticosteroid may be dexamethasone. Where the compound is a chelating agent, the chelating agent may be desferrioxamine. Where the compound is an anti-inflammatory drug, the anti-inflammatory drug agent may be curcumin, aspirin, eicosapentaenoic acid, or docosahexaenoic acid. The compound may be loaded into the microsphere (intracapsular microsphere) at a drug load of between 1% and 20% or between 5 and 10% w/v. The microsphere may have a dimension of between 1 μm to about 300 μm, or between 10 μm to about 100 μm, and may be selected for release of the compound over a particular time period, such as, for example, 21 days.

The microcapsule may be formed by a process comprising a microencapsulation technique resulting in formed dimensions of between 300 μm and 2000 μm. The microencapsulation technique may be a vibrational nozzle technique, and the interior core may be formed by, in one embodiment, injecting or spraying an interior core mixture comprising the live cell at between $1\times10^3$ and $1\times10^5$ cells/ml, the second polymer, wherein the second polymer comprises alginate at 0.8% to 2.0% (w/v), and the microspheres at between 0.5 and 15 mg/ml through a vibrational nozzle. The outer shell of the microcapsule may be formed by simultaneously injecting or spraying the interior core solution with a first polymer solution comprising an alginate solution which has been filtered through a membrane through the vibrational nozzle. The first polymer solution may include an alginate solution has been filtered through a 1 to 0.1 micron filter, and the alginate solution is at between about 5% and 0.5% (w/v), and the filter may be selected from a 0.8 micron, a 0.45 micron, or a 0.22 micron filter, and the alginate solution may be 1.0% w/v, 1.2% (w/v), 1.5% (w/v), or 2.0% (w/v). The formed microcapsules may be hardened by addition of a calcium ion, a divalent cation or a combination thereof.

Prior to use, the formed, hardened microcapsules may be is stored RPMI-1640 comprising 10% FBS and 1% pen/strep at 37° C. In one embodiment, the cells are pancreatic islet cells and the islet cells encapsulated in the microcapsules of the invention exhibit survival of at least 70%, at least 80% at day 10 of incubation in RPMI-1640 comprising 10% FBS and 1% pen/strep at 37° C.; or survival of at least 50% or 60% at day 21 of incubation in RPMI-1640 comprising 10% FBS and 1% pen/strep at 37° C.

The methods of the invention also include a method for producing microcapsules providing improved survival and/or function for an encapsulated cell. The method includes the steps of preparing an outer shell solution comprising a first polymer; preparing an interior core solution comprising a second polymer and a live cell; And preparing a microsphere solution comprising a third polymer and a compound capable of improving survival of the at least one cell. The method also includes the steps of combining the microsphere solution with the interior core solution to form a mixed interior core solution; and contacting the mixed interior core solution with the outer shell solution to form the microcapsules. The formed microcapsules have improved survival and/or improved function compared to a live cell in a microcapsule in the absence of the compound capable of improving survival of the at least one cell.

In one embodiment, the contacting step comprises injecting the mixed interior core mixture comprising the live cell at between $1\times10^3$ and $1\times10^5$ cells/ml, the second polymer comprising alginate at 0.8% to 2.0% (w/v), and the microsphere solution at between 0.5 and 15 mg/ml simultaneously with the outer shell solution comprising the first polymer comprising alginate at between 0.5% and 5% through two vibrational nozzles.

The method also includes an insulin-producing system; a method of delivery of insulin to a patient in need thereof, comprising a microcapsule made by the methods of the invention, or microcapsules of the invention.

The present invention also includes a method to treat treatment for diabetes and diabetic-related conditions, comprising administering an effective amount of the microcapsule made by the methods of the invention, or a microcapsule of the invention, to the patient. The diabetic condition can be prediabetes or diabetes mellitus.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

The features, objects and advantages other than those set forth above will become more readily apparent when consideration is given to the detailed description below. Such detailed description makes reference to the following drawings, wherein:

(FIG. 4A) Viability of porcine islets in AL and AL-extMS microcapsules versus time. (FIG. 4B) Stimulation index (SI) of the islets encapsulated in the AL and AL-extMS capsules. Data are represented as mean±SD. *denotes a statistically significant difference in islet viability or SI between the AL and AL-extMS capsules, *p<0.05, p<0.005 and *p<0.001.

Figure 1A:
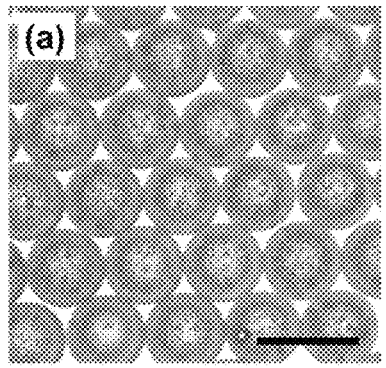
FIG. 1A-1E. Optical (top layer) and SEM images (bottom layer) of PLGA MSs loaded with (FIG. 1A, 1D) 0, (FIG. 1B, 1E) 5, and (FIG. 1C) 10% (w/w) exenatide. Scale bar=50 μm.
Figure 1B:
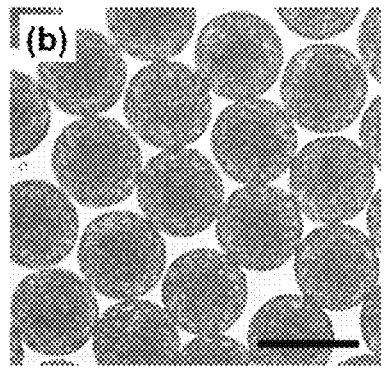
Figure 1C:
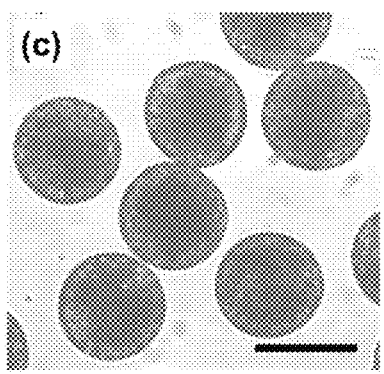
Figure 1D:
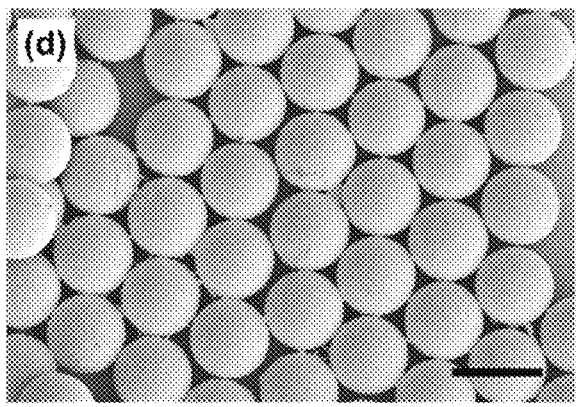
Figure 1E:
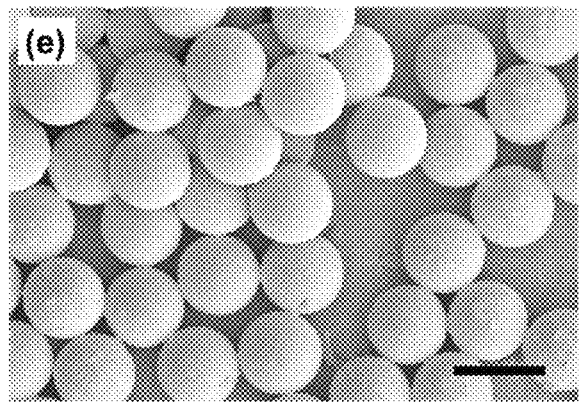

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION OF THE INVENTION

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

In the present invention, in one embodiment, the present invention demonstrates a beneficial effect of sustained on-site release of exenatide on the survival and function of encapsulated islets, employing exenatide-loaded PLGA microspheres (MSs). The PLGA MSs were monodisperse, exhibiting sustained exenatide release during the 21-day period with minimal initial burst. The porcine islets co-encapsulated with the exenatide-loaded PLGA MSs in alginate microcapsules showed improved viability and GSIS function. This implies that the microsphere-mediated on-site release of exenatide could provide potential benefits to islet transplantation, especially during the early post-transplantation period lacking vasculature, while mitigating the adverse effects of systemic exenatide.

Accordingly, the present invention generally relates to a compositions, methods of making a composition, compositions made by the method, and methods of use of the compositions, related to microcapsules for improved survival and/or function of encapsulated live cells. The compositions, in broad scope, include an outer shell which includes a first polymer, as well as an interior core which includes at least one live cell, a second polymer; and at least one microsphere. The microspheres themselves include a third polymer together with a compound capable of improving survival of the at least one cell. These compositions provide the advantage of allowing for improved survivability and/or function to the encapsulated at least one live cell compared to a live cell in a microcapsule in the absence of the compound capable of improving survival of the at least one cell.

Thus, in one aspect, the present invention also provides a method for producing a microcapsule, which provides improved survival and/or function for an encapsulated live cell. The method includes the step of preparing an outer shell solution comprising a first polymer and preparing an interior core solution comprising a second polymer and a live cell. In another step, a microsphere solution is prepared, wherein the microsphere solution comprises a third polymer and a compound capable of improving the survival and/or function of the at least one live cell. The microsphere solution and the interior core solution are combined and/or mixed to form a mixed interior core solution. The mixed interior core solution is contacted with the outer shell solution to form the microcapsules, where the live cell in the microcapsules has improved survival and/or improved function compared to a live cell in a microcapsule in the absence of the compound capable of improving survival of the at least one cell. Methods, compositions, and uses of the instant invention are described in more detail hereinbelow.

The compositions of the invention may additionally comprise nutritional additives and components that can help improve and preserve function of the cells to allow for improved activity, stability, and release of the cells. This may include buffers to stabilize pH, bulking agent, salt, tonicity adjusters, such as mannitol, sucrose, glycine, glycerol, PEG and other polyhydric alcohols, amino acids such as glycine, L-serine, alanine, proline, phenylalanine, arginine, proline, sodium chloride, and additional nutrients for improved survival and activity.

Microspheres

In one embodiment, the compositions comprise an interior core which includes at least one microsphere. The microspheres themselves may comprise a third polymer together with a compound capable of improving survival of the at least one cell. The compound capable of improving the survival of the at least one cell can be any compound that promotes survival of a cell, and may be specific to cell type.

When the cell type is a pancreatic islet cell, the compound capable of improving survival of the at least one cell may include one or more of a glucagon-like peptide-1 (GLP-1) receptor agonist, an anti-inflammatory drug, a pro-angiogenic drug, a chelating agent, and a corticosteroid.

Incretins are hormones that stimulate insulin secretion in response to meals. The two most important incretin hormones are called glucagon-like peptide-1 (GLP-1) and glucose-dependent insulinotropic polypeptide (GIP). Glucagon-like peptide 1 (GLP-1) binds to the GLP-1 receptor on pancreatic islet cells (beta cells). GLP-1 and its analogs have been shown to increase insulin production by beta cells in response to glucose, as well as promote beta cell regeneration, protect from apoptosis, and interfere with the autoimmune attack on beta cells. Incretin mimetics like exenatide are a potentially useful treatment in combination with islet cell transplantation. The art shows that exenatide treatment in combination with islet cell transplantation may result in improved long-term islet graft function.

The art demonstrates a number of known analogs to GLP-1, e.g., GLP-1 receptor agonists. In one embodiment, a GLP-1 receptor agonist can include exenatide, exendin-4, truncated exendin-4, esterified exendin-4, N-alkyl exendin-4, PEG-modified exendin-4, liraglutide, lixisenatide, dulaglutide, taspoglutide, and semaglutide.

In one embodiment, the GLP-receptor agonist is exenatide, a known incretin mimetic, which is a synthetic form of the naturally occurring exendin-4 isolated from the saliva of the Gila monster (*Heloderma suspectum*). It is a 39-amino acid peptide, which shares 53% of its amino acid sequence identity with human glucagon-like peptide-1 (GLP-1), and both have common glucoregulatory actions.

Where the compound is a corticosteroid, the corticosteroid may be dexamethasone. Where the compound is a chelating agent, the chelating agent may be desferrioxamine.

Where the compound is an anti-inflammatory drug, the anti-inflammatory drug agent may be curcumin, aspirin, eicosapentaenoic acid, or docosahexaenoic acid.

Exenatide only has a short plasma half-life of 2.4 hours and an action time of about 8 hours. To obtain a more sustained systemic release of exenatide, the art shows that microsphere formulations have been developed and the safety, reliability, and efficiency of microspheres have been well established over the years. Currently, a long-acting exenatide product on the market in microsphere form is Bydureon™ (Amylin Pharmaceuticals).

In one embodiment, the compound capable of improving survival of the cell is within a microsphere comprising a third polymer. In some embodiments, the third polymer comprises a polymer selected from one or more of poly (glycolic acid), poly(lactic acid), poly(lactic-co-glycolic acid) (PLGA) and their copolymers, poly(ester amides), poly(ε-caprolactones) (PCL) and their copolymers, polyurethanes, polymethacrylates, poly(anhydrides), poly(phosphoesters) and their copolymers. In one embodiment, the third polymer comprises poly(lactic-co-glycolic acid) (PLGA).

Generally, the compound is loaded onto the surface of or into the microsphere, which then releases it as the matrix materials degrade. In one embodiment, to create the microspheres, a water-in-oil (W/O) solvent evaporation method is employed. Generally speaking, exenatide is dissolved in a water phase then mixed with a dichloromethane solution containing PLGA as known in the art. Thus, in one embodiment, the microspheres further include a polymer or mixture of polymers. A number of synthetic polymers have been investigated for in vivo delivery, including the biodegradable polymer poly(dl-lactic acid-co-glycolic acid) (PLGA). PLGA is frequently used, as the degradation rate of the polymer can be controlled and it has FDA approval for certain clinical applications. The versatility of chemically synthesized polymers such as PLGA allows for the fabrication of scaffolds with different porosities and mechanical properties, depending on the application. Microspheres can be fabricated using a variety of different biodegradable polymers such as chitosan, gelatin and PLGA, and their use for delivery of cells and growth factors for repair of tissues such as bone, skin and brain has been reported.

PLGA polymers are a copolymer based on lactic acid and glycolic acid, and which may include small amounts of other comonomers that do not substantially affect the advantageous results that can be achieved in accordance with the present invention. As used herein, the term "lactic acid" includes the isomers L-lactic acid, D-lactic acid, DL-lactic acid and lactide, while the term "glycolic acid" includes glycolide. Most preferred are poly(lactide-co-glycolide)copolymers, commonly referred to as "PLGA." The polymer may have a monomer ratio of lactic acid/glycolic acid of from about 100:0 to about 15:85, preferably from about 75:25 to about 30:70, more preferably from about 60:40 to about 40:60, and an especially useful copolymer has a monomer ratio of lactic acid/glycolic acid of about 50:50.

As indicated in U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 8,000, 10,000, 30,000 and 100,000 are available from Boehringer Ingelheim (Petersburg, Va.), Medisorb Technologies International L.P. (Cincinnati, Ohio) and Birmingham Polymers, Inc. (Birmingham, Ala.) as described below. U.S. patents noted herein are incorporated by reference in their entireties for all they teach and disclose.

Examples of polymers include, but are not limited to, Poly (D,L-lactide) Resomer® L104, PLA-L104, code no. 33007, Poly (D,L-lactide-coglycolide) 50:50 Resomer® RG502, code 0000366, Poly (D,L-lactide-coglycolide) 50:50 Resomer® RG502H, PLGA-502H, code no. 260187, Poly (D,L-lactide-co-glycolide) 50:50 Resomer® RG503, PLGA-503, code no. 0080765, Poly (D,L-lactide-co-glycolide) 50:50 Resomer® RG506, PLGA-506, code no. 95051, Poly (D,L-lactide-co-glycolide) 50:50 Resomer® RG755, PLGA-755, code no. 95037, Poly L-Lactide MW 2,000 (Resomer® L 206, Resomer® L 207, Resomer® L209, Resomer® L 214); Poly D,L Lactide (Resomer® R 104, Resomer® R 202, Resomer® R 203, Resomer® R 206, Resomer® R 207, Resomer® R 208); Poly L-Lactide-co-D,L-lactide 90:10 (Resomer® LR 209); Poly glycolide (Resomer® G 205); Poly D,L-lactide-co-glycolide 50:50 (Resomer® RG 504H, Resomer® RG 504, Resomer® RG 505); Poly D-L-lactide-co-glycolide 75:25 (Resomer® RG 752, Resomer® RG 756); Poly D,L-lactide-co-glycolide 85:15 (Resomer® RG 858); Poly L-lactide-co-trimethylene carbonate 70:30 (Resomer® LT 706); Poly dioxanone (Resomer® X 210) (Boehringer Ingelheim Chemicals, Inc., Petersburg, Va.). Additional examples of appropriate polymers include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cinciinatti, Ohio); and Poly D,L-lactide-co-glycolide 50:50; Poly D,L-lactideco-glycolide 65:35; Poly D,L-lactide-co-glycolide 75:25; Poly D,L-lactide-coglycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

Microsphere Fabrication

A number of methods are known to encapsulate hydrophilic drugs into polymer microspheres, e.g., PLGA microspheres. In one method of the invention the hydrophilic drug (here, a compound capable of improving the survival of the at least one cell; in one embodiment, exenatide) can dissolved in water or aqueous solution. In one embodiment, the aqueous solution can comprise polyvinyl alcohol. The polymer, such as PLGA can be dissolved in a water-immiscible solvent, such as, for example, dichloromethane. The aqueous phase comprising the compound of the invention can then be emulsified in the polymeric (e.g., PLGA) organic solution. This primary emulsion may then mixed again in an emulsifier-containing aqueous phase, such as an aqueous solution comprising polyvinyl alcohol. The microspheres may be further treated to result in the desired physical dimensions, hardened, and washed have the organic solvent removed.

For microsphere polymer delivery systems, the properties pertaining to the polymer, parameters such as drug loading, internal aqueous volume, surfactant concentration and preparation method can be manipulated to affect the drug release behavior, as known in the art, and as explained further herein.

In one embodiment, the compound capable of improving survival of the at least one cell is loaded into the intracapsular microspheres at between 1% and 20%. In another embodiment, the compound capable of improving survival of the at least one cell is loaded into the intracapsular microspheres at between 5 and 10% w/v. Calculation of drug loading and encapsulation efficiency is known in the art. For example, Where $C_R$ is the drug concentration of the release medium, $V_R$ is the volume of the release medium, $m_{mp}$ is the mass of the microparticles and $m_D$ and $m_{PLGA}$ are, respectively, the mass of drug and mass of PLGA initially added during particle synthesis.

Drug loading % $DL=(C_R V_R/m_{mp}) \times 100$

Encapsulation efficiency % $EE=((C_R V_R/m_{mp})/(m_D/(m_D+m_{PLGA}))) \times 100$.

Table 1 summarizes the drug loading, loading efficiency and size of an embodiment comprising exenatide-loaded PLGA microspheres. The loading efficiency was 85% for a 5% theoretical loading, which decreased to 80% as the loading increased to 10%, while the size increased with the exenatide loading.

TABLE 1

Drug loading and loading efficiency of exenatide-loaded PLGA MSs

| Theoretical loading [%, w/w] | Drug loading[a] [%, w/w] | Loading efficiency[b] [%] | Microsphere size Mean diameter ± SD [μm] |
|---|---|---|---|
| 0 | 0 | 0 | 40.92 ± 0.83 |
| 5 | 4.20 ± 0.25 | 84.06 ± 5.09 | 45.41 ± 0.97 |
| 10 | 7.91 ± 0.55 | 79.08 ± 5.50 | 51.67 ± 1.10 |

[a] Drug loading (%, w/w) = $\frac{\text{Weight of exenatide in microspheres}}{\text{Weight of exenatide - loaded microspheres}} \times 100$

[b] Loading efficiency (%) = $\frac{\text{Drug loading}}{\text{Theoretical loading}} \times 100$ In order to form the microspheres of the desired physical dimensions and quality, precision particle fabrication (PPF) may be used. PPF technology also allows fabrication of predefined particle size distributions via continuous variation of the process parameters. Such a technique is disclosed in, for example, U.S. Pat. No. 8,293,271, issued Jun. 9, 2009, and U.S. Pat. No. 8,663,511, issued Mar. 4, 2014, both entitled "Encapsulated materials and methods for encapsulating materials," inventors Kim, Kyekyoon and Choi, Hyungsoo, which are incorporated by reference herein in their entireties for all that is taught and disclosed. U.S. Pat. Nos. 8,663,511 and 8,293,271 both teach a system which provides a method for applying a force to an inner stream, an outer stream or both of a combined stream to produce of plurality of capsules (e.g., microcapsules). The method generally comprises spraying a polymer-containing solution through a nozzle with (i) acoustic excitation to produce uniform droplets and (ii) an annular, non-solvent carrier stream allowing further control of the droplet size. The apparatus for carrying out the method is designed to pass a solution carrying the emulsified microspheres to form a smooth, cylindrical jet. The nozzle is vibrated by a piezoelectric transducer driven by a wave generator at a frequency tuned to match the flow rate and desired drop size. The acoustic wave along the liquid jet generates periodic instabilities which in turn, break the stream into a train of uniform droplets.

The inventors found, that in one embodiment of particle-mediated drug delivery, particle size plays an important role, influencing the encapsulation efficiency, intraparticle drug distribution and diffusive drug release, thus the drug-release kinetics. The PPF method as disclosed in the present invention allows for production of monodisperse PLGA microspheres, which provides for predictable drug (e.g., exenatide) release without the uncertainties resulted from size nonuniformity in the microspheres.

In one embodiment, the microspheres' dimension is selected for release of the compound over a particular time period. The time period may correspond to the time required for revascularization or partial revascularization of the cells (e.g., islet cells) after implantation. In one embodiment, the time period is about 5 days, about 10 days, about 15 days, about 18 days, about 20 days, about 21 days, about 22 days, about 25 days, about 30 days, about 35 days, or about 40 days.

Accordingly, in one embodiment, the microspheres of the invention are fabricated by the PPF method (or, an alternative method) to have a mean dimension of between about 1 μm to about 300 μm; between about 10 μm to about 250 μm; between about 20 μm to about 200 μm; between about 25 μm to about 100 μm; between about 30 μm to about 75 μm; between about 35 μm to about 60 μm; between about 40 μm to about 55 μm; or, between about 10 μm to about 100 μm; between about 20 μm to about 80 μm. The mean dimension may have a standard deviation of between about 0.1 μm to about 5 μm; between about 0.2 μm to about 10 μm; between about 0.3 μm to about 5 μm; between about 0.4 μm to about 3 μm; between about 0.5 μm to about 2 μm; or less than 5 μm, less than 4 μm; less than 3 μm, less than 2 μm; less than 1.5 μm, less than 1 μm. The lower the standard deviation, the less nonuniformity in microsphere size.

Figure 2:
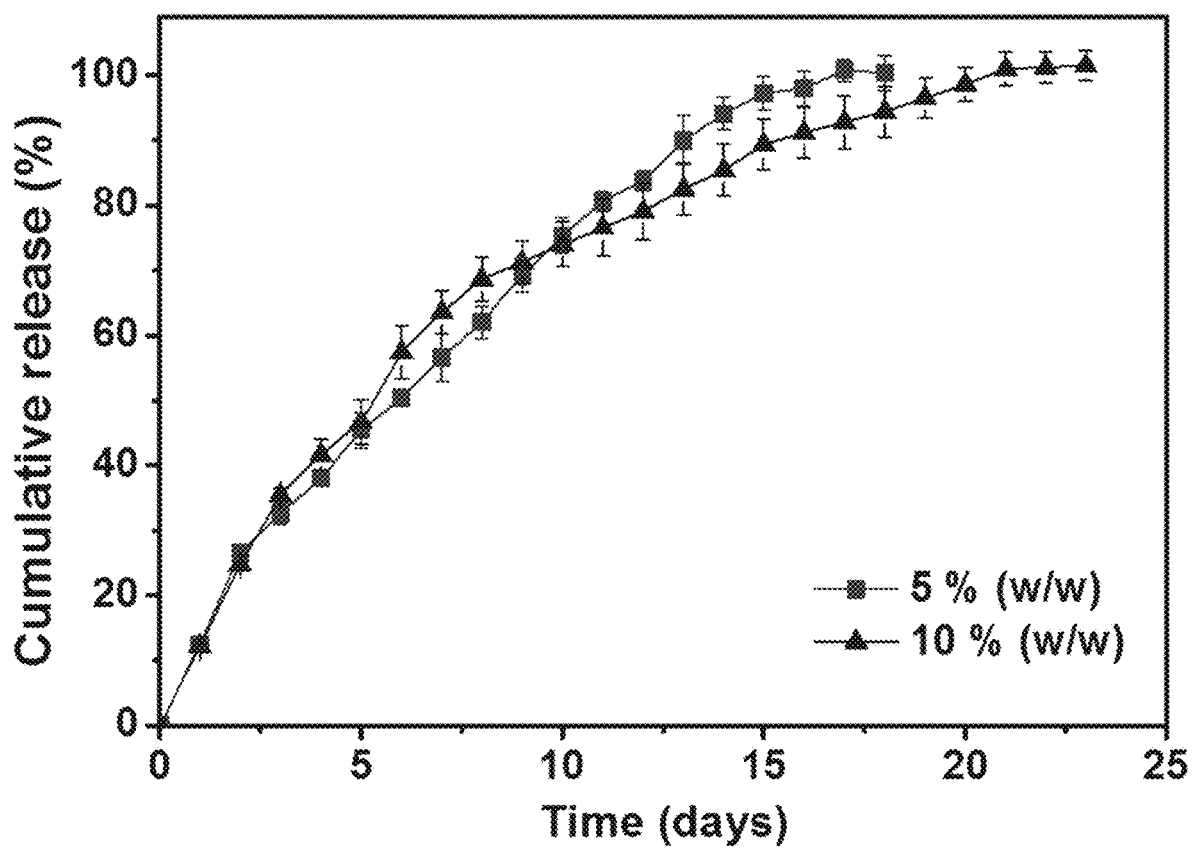
FIG. 2. In vitro cumulative drug release profiles of the exenatide-loaded PLGA MSs with 5 and 10% (w/w) exenatide. Data are represented as mean±SD (n=4).

In one embodiment, the microspheres of the invention exhibit dense and smooth surface morphology and size uniformity with small coefficients of variation (<2.2%). In this embodiment, the PLGA microspheres were monodisperse, exhibiting sustained exenatide release during the 21-day period with minimal initial burst. FIG. 2 shows the drug release profiles of an embodiment of PLGA microspheres with 5 and 10% (w/w) theoretical loadings of exenatide. The exenatide-loaded microspheres exhibited a low initial release, i.e., 11-13%, within 24 h compared to the burst release, i.e., 11-65%, reported by others, showing the advantages of the present invention. The minimal burst release exhibited by the PLGA microspheres could be attributed to the controlled generation of the liquid drops, stable positioning and small volume of the internal water phase, and formation of dense microsphere surface during the solidification process. Cumulative 100% release from the 5 and 10% (w/w) exenatide-loaded microspheres was achieved in 17 and 22 days, respectively.

As an example of the fabrication of exenatide-loaded PLGA microspheres of the present invention fabricated by the PPF method, the following protocol was used. Briefly, a desired amount of exenatide was dissolved in a 1% (w/v) PVA solution, added to a 5% (w/v) PLGA solution in dichloromethane (DCM) and emulsified by sonication for 30 s. The emulsion and 1% (w/v) PVA solution were fed into the coaxial nozzle and broken up into uniform droplets by acoustic excitation. The resulting droplets were collected in a bath containing a 1% (w/v) PVA solution and hardened. Thus-obtained MSs were washed three times with deionized water, freeze-dried, and stored in a sealed tube at −20° C. The morphology of the PLGA microspheres with 0, 5, and 10% (w/w) loadings was observed by optical and scanning electron microscopy and shown in FIG. 1 which confirms a dense and smooth surface morphology and size uniformity with small coefficients of variation (<2.2%).

Interior Core

The compositions, in broad scope, also include an outer shell which includes a first polymer, as well as an interior core which includes at least one live cell, a second polymer; and at least one microsphere.

Cells can be defined as the smallest structural and functional unit of an organism, typically microscopic and consisting of cytoplasm and a nucleus enclosed in a membrane. There are two distinct types of cells: prokaryotic cells (e.g. bacterial cells) and eukaryotic cells (e.g. plant, fungal or animal cell). A well-defined nucleus surrounded by a membranous nuclear envelope is present only in eukaryotic cells. Cells can include animal, plant and fungal cells, including those in tissue culture. Cells contemplated for use herein include, without limitation, all eukaryotic cells, as described hereinbelow.

In one embodiment, the invention relates to encapsulation of pancreatic islet cells. Generally, use of pancreatic islet transplantation has gradually showed satisfactory and prospective application in the treatment of type 1 diabetes mellitus (T1DM.) Islet allotransplantation had achieved a remarkable success, but shortage of donors still prevented the progression of clinical islet transplantation. Xenotransplantation provides an effective and appropriate solution for this limitation. Although encouraging findings have been obtained in pig-to-primate islet xenotransplantation, the potential clinical application of pig islet still faces two major challenges: inadequate supply of islet cells of high quality and xenorejection.

Methods of isolating pancreatic islet cells for use in transplanting, as well as methods for encapsulating pancreatic islet cells, are known in the art. Field et al., *Transplantation* 61:1554 (1996); Linetsky et al., *Diabetes* 46:1120 (1997); Ricordi et al. (1986) A method for the mass isolation of islets from the adult pig pancreas. *Diabetes* 35, 649-653. Fresh pancreatic tissue can be divided by mincing, teasing, comminution and/or collagenase digestion. The islets are then isolated from contaminating cells and materials by washing, filtering, centrifuging or picking procedures. Methods and apparatus for isolating and purifying islet cells are described in U.S. Pat. Nos. 5,447,863, 5,322,790, 5,273,904, and 4,868,121. The isolated pancreatic cells may optionally be cultured prior to encapsulation, using any suitable method of culturing islet cells as is known in the art. See e.g., U.S. Pat. No. 5,821,121. Isolated cells may be cultured in a medium under conditions that helps to eliminate antigenic components (Transplant. Proc. 14:714-23 (1982)). The isolated cells may be genetically engineered to improve function, or may be derived from differentiation of stem cells and islet precursors. In one embodiment, the isolated cells are xenogeneic. In another embodiment, the isolated cells are porcine.

Although the inventors provided results with islet cells, other cell types can be used in the capsules of the present disclosure, being encapsulated within a capsule having a plurality of microspheres that can release a compound to aid in the survival and/or function of the particular cell, promoting the release of beneficial components excreted by the particular cell. In some embodiments, the live cell can include a pancreatic islet cell, a primary liver cell (hepatocyte), a mesenchymal stem cell, a neuron, or a fibroblast. In one embodiment, the live cell is a porcine pancreatic islet cell.

In another embodiment, the cell may be a therapeutically engineered cell and/or stem cell. Encapsulation of these cells may help to provide a physical barrier to protect the cells from hostile extrinsic factors and significantly improve the therapeutic efficacy of transplanted stem cells in different models of disease, such as cancer. Methods and microcapsules of the present invention may also be useful for developing stable encapsulated vaccines, stable encapsulated protein therapeutics, and DNA encapsulation.

The interior core may be formed by forming a solution comprising the cell and the polymer. In one embodiment, the cell in the solution is at a concentration of between $0.01 \times 10^3$ and $100 \times 10^6$ cells/ml, although the amount used will vary based on the concentrations and amounts desired. Concentrations of between about $0.01 \times 10^3$ and $100 \times 10^6$ cells/ml, $0.1 \times 10^3$ and $10 \times 10^6$ cells/ml, $1 \times 10^3$ and $1 \times 10^6$ cells/ml, or $5 \times 10^3$ and $0.1 \times 10^6$ cells/ml may also be used. A single cell or clusters of cells can occur per microcapsule.

As known in the art, the encapsulation and eventual release of "payload" of the microcapsule may be determined an array of factors including the type of polymer, the polymer molecular weight, the copolymer composition, the nature of any excipients added to the microsphere formulation (e.g., for stabilization of the therapeutics), and the microsphere size. The type of polymer used in microsphere fabrication and the way in which the polymer degrades affect release rate. Bulk-eroding polymers, such as PLGA, readily allow permeation of water into the polymer matrix and degradation throughout the microsphere matrix. Polymer molecular weight can affect polymer degradation and drug release rates. Increase in molecular weight decreases diffusivity and therefore release rates. Diffusion through water-filled pores occurs as polymer degradation generates soluble monomers and oligomers that can diffuse out of the particle. These small products are formed more quickly upon degradation of lower molecular weight polymers. The size of the microcapsule will also affect rate of release, since as size decreases, surface to volume ratio of the particles increases allowing for greater flux from the particle. Water penetration will occur more quickly due to the shorter distance into the center of the particle.

In one embodiment, the microcapsules of the present invention were found to have a size, by optical micrograph, of 411 μm±11.6 μm mean diameter and were produced from a 2% alginate solution for the shell and 1.5% alginate core solution comprising islet cells ($1 \times 10^4$ cells/ml) and microspheres (1.5 mg/ml) for the core. The smaller microcapsules are more likely to maintain cell viability due to lower resistance to transport of oxygen, nutrients, and metabolites, and possess greater mechanical strength and higher biocompatibility.

In the instant invention, the microcapsules of the instant invention may be formed such that they are between about 50 µm and about 5,000 µm, between about 100 µm and 1,000 µm, between about 200 µm and about 800 µm, between about 300 µm and about 600 µm; between about 350 µm and about 500 µm; or between about 400 µm and about 450 µm.

Polymers for use in the instant invention (for the first polymer and the second polymer) may include any number of polymers known in the art, including polymers that are capable of forming hydrogels. Such polymers include polysaccharides such as alginate, cellulose, cellulose derivatives such as ethyl cellulose, hydroxypropyl methylcellulose and the like; hyaluronic acid, chitosan, agarose; polyethers such as polyethylene glycol, polypropylene glycol and copolymers such as polylysine, polycaprolactone, polylactide and the like; poly($\alpha$-hydroxy esters) such as poly(L-lactic-co-glycolic acid), poly($\varepsilon$-caprolactone), poly(NiPAAm), poly(vinyl alcohol); polyvinyl alcohol copolymers (such as with acrylate or methacrylate); polyurethane and the like; and proteins such as collagen, fibrin glue, and gelatin.

Alginate is a well-known example of a polymer useful for the microcapsules of the present invention. It is a polysaccharide with mannuronic and glucuronic acid residues and can be crosslinked by calcium ions. Crosslinking can be carried out at room temperature and physiological pH. Alginates may also include modified alginate-starch polymer, alginate-inulin-xanthan gum, alginate and poly L-lysine polymer a chitosan/alginate polymer and a chitosan/xanthan polymer. Numerous examples of such alginate encapsulation materials are disclosed in, e.g., International patent application WO 2012/101167 which is incorporated herein by reference its entirety for all that is taught and disclosed. In some embodiments the alginate comprises an alginate derived from brown sea algae such as, for example, Protanal™ LF 120 (LF 120) derived from *Laminaria hyperborea*, alginate Protanal™ LF 20/60 (LF 20/60) derived from *Laminaria hyperborea*, alginate MVG™ (MVG) derived from *Laminaria hyperborea*, alginate Pronatal™ HF 120 (HF 120) derived from *Laminaria hyperborea*, alginate Pronatal™ SF 120 (SF 120) derived from *Laminaria hyperborea*, alginate Pronatal™ SF 120 RB (SF 120 RB) derived from; *Laminaria hyperborea*, alginate Pronatal™ LF 200 RB (LF 200 RB) derived from *Laminaria hyperborea*, alginate Manugel™ DMB (DMB) derived from *Laminaria hyperborea*, Keltone™ HVCR (HVCR) derived from *Macrocystis pyrifera*, and Keltone™ LV (LV) derived from *Macrocystis pyrifera*.

The concentration of polymer in the solution may be optimized for the particular application. Therefore, in one embodiment of the instant invention, the polymer is alginate. As stated above, alginate may be advantageously hardened by crosslinking after formation of the particles by treatment with divalent ion, such as calcium ion, as known in the art. Such a gel formation occurs mainly at the junctions between ions and homopolymeric blocks of glucuronic acid. Since calcium-alginate gel produced through this process has bridges formed by ion bond, it can make hard hydrogel. Alginate gel can be prepared in aqueous solutions and also swelled and gradually biodegraded.

When alginate is used as the first and the second polymer, alginate may be used at concentrations independently between about 0.1% (w/v) and 10% (w/v), between about 0.5% (w/v) and 5% (w/v), at about between about 0.8% to 2.0% (w/v). The concentrations of alginate in the core solution and the outer shell solution may differ from one another to form a shell having differential properties from the core. For example, the shell solution may be between 1 and 3% alginate, optionally, about 2% and the core solution may be between about 0.5 and 2%, optionally, about 1.5% alginate. The porosity of the alginate used for the present invention may be controlled and made consistent by filtering the alginate through a filter, such as 1 to 0.1 micron filter. Typical pore sizes for filtration of the alginate are 0.8 micron, a 0.45 micron, or a 0.22 micron filter.

Optionally, a solution comprising alginate may comprise further polymers, water-soluble filler or gel extender such as, for example, a 0-30% aqueous solution of a polysaccharide such as dextran. Other suitable filler materials include sodium carboxy methyl cellulose, methyl cellulose, dextrins, and some soluble starches.

Outer Shell

The outer shell, in some embodiments, may be formed by preparing a solution comprising the polymer. The polymer and concentrations of the polymer may be prepared in accordance with the guidelines above set out for the interior core, with the difference that the outer shell will in many embodiments have a higher concentration of polymer (w/v) than the interior core. In one embodiment, the microcapsules of the present invention may include wherein the first and second polymer are comprise alginate.

Microcapsule Encapsulation Techniques

In one aspect, the present invention also provides a method for producing a microcapsule, which provides improved survival and/or function for an encapsulated live cell. The method includes the step of preparing an outer shell solution comprising a first polymer and preparing an interior core solution comprising a second polymer and a live cell. In another step, a microsphere solution is prepared, wherein the microsphere solution comprises a third polymer and a compound capable of improving the survival and/or function of the at least one live cell. The microsphere solution and the interior core solution are combined and/or mixed to form a mixed interior core solution. The mixed interior core solution is contacted with the outer shell solution to form the microcapsules, where the live cell in the microcapsules has improved survival and/or improved function compared to a live cell in a microcapsule in the absence of the compound capable of improving survival of the at least one cell. Methods, compositions, and uses of the instant invention are described in more detail hereinbelow.

The present methods can include the step of encapsulating a live cell. Specifically, the encapsulated live cell may be encapsulated by one of any number of a variety of encapsulation techniques. Encapsulation techniques for live cells are generally known in the art. Such encapsulation techniques include combinations of phase separation or precipitation, emulsion/solvent evaporation, and/or spraying methods. Variations of the fabrication parameters during the encapsulation technique, as known in the art, generally allow control of the particle size and size distribution. Encapsulation techniques for encapsulating a live cell include a physicochemical or mechanical process to entrap the live in a material in order to produce particles with diameters of a few nanometers to a few millimeters. Thus microcapsules are small particles that contain an active agent or core material surrounded by a coating or shell. In one embodiment a microcapsule of the invention is a small sphere with a uniform wall around it. The material inside the microcapsule is referred to as the core, internal phase, or fill, whereas the wall is sometimes called a shell, coating, or membrane. Some materials like lipids and polymers, such as alginate, may be used as a mixture to trap the material of interest inside the core.

Briefly, encapsulation techniques include pan coating, where the cores are tumbled in a pan while the coating is applied, or air coating, where a solid particulate core is dispersed into an airstream and coated with polymers in a volatile solvent. Encapsulation techniques also include wherein liquids may be encapsulated by using a rotating extrusion head containing concentric nozzles with a jet of core liquid surrounded by a sheath of shell solution; as the jet moves through the air it breaks and is coated with the shell solution. Encapsulation techniques also include use of vibrational nozzle techniques which include using a laminar flow through a nozzle with vibration of the nozzle or liquid in resonance with Rayleigh instability to break the stream into individual microparticles.

In one embodiment, the encapsulated live cell(s) of the invention may be created by an encapsulation technique comprising a microcapsule fabrication technology which combines two techniques for generating monodisperse microcapsules with precisely controlled sizes. This precision particle fabrication (PPF) technology also allows fabrication of predefined particle size distributions via continuous variation of the process parameters. Such a technique is disclosed in, for example, U.S. Pat. No. 8,293,271, issued Jun. 9, 2009, and U.S. Pat. No. 8,663,511, issued Mar. 4, 2014, both entitled "Encapsulated materials and methods for encapsulating materials," inventors Kim, Kyekyoon and Choi, Hyungsoo, which are incorporated by reference herein in their entireties for all that is taught and disclosed. U.S. Pat. Nos. 8,663,511 and 8,293,271 both teach a system which provides a method for applying a force to an inner stream, an outer stream or both of a combined stream to produce of plurality of capsules (e.g., microcapsules). The method generally comprises spraying or injecting a polymer-containing solution through a nozzle with (i) acoustic excitation to produce uniform droplets and (ii) an annular, non-solvent carrier stream allowing further control of the droplet size. The apparatus for carrying out the method is designed to pass a solution carrying the desired component(s), through a small nozzle or other orifice (20 µm to a few mm in diameter) to form a smooth, cylindrical jet. The nozzle is vibrated by a piezoelectric transducer driven by a wave generator at a frequency tuned to match the flow rate and desired drop size. The acoustic wave along the liquid jet generates periodic instabilities which in turn, break the stream into a train of uniform droplets.

The method may include the step of preparing an interior core solution comprising a second polymer and a live cell and combining the interior core solution with the microsphere solution. The microsphere solution is prepared as discussed elsewhere herein.

The interior core solution may be formed by forming a solution comprising the cell and the polymer. In one embodiment, the prepared and pelleted cells may be resuspended in the polymer solution. In one embodiment, the cell in the interior core solution is at a concentration of between $0.01 \times 10^3$ and $100 \times 10^6$ cells/ml, although the amount used will vary based on the concentrations and amounts desired. Concentrations of between about $0.01 \times 10^3$ and $100 \times 10^6$ cells/ml, $0.1 \times 10^3$ and $10 \times 10^6$ cells/ml, $1 \times 10^3$ and $1 \times 10^6$ cells/ml, or $5 \times 10^3$ and $0.1 \times 10^6$ cells/ml may also be used. A single cell or clusters of cells can occur per microcapsule. When alginate is used as the second polymer, alginate may be used in the interior core solution at concentrations independently between about 0.1% (w/v) and 10% (w/v), between about 0.5% (w/v) and 5% (w/v), at about between about 0.8% to 2.0% (w/v). The concentrations of alginate in the interior core solution and the outer shell solution may differ from one another to form a shell having differential properties from the core. For example, the outer shell solution may be between 1 and 3% alginate, optionally, about 2% and the interior core solution may be between about 0.5 and 2%, optionally, about 1.5% alginate. The porosity of the alginate used for the present invention may be controlled and made consistent by filtering the alginate through a filter, such as 1 to 0.1 micron filter. Typical pore sizes for filtration of the alginate are 0.8 micron, a 0.45 micron, or a 0.22 micron filter.

In order to produce a mixed interior core solution, a microsphere solution as prepared by methods described elsewhere herein can be added to the interior core solution at 1.5 mg/ml to create a mixed interior core solution. The addition step may be carried out by any method known in the art, but gentle forms of mixing as known in the art are useful to preserve the structural integrity of the cells and the microspheres. The outer shell solution may be formed as disclosed elsewhere herein.

To fabricate uniform core-shell microcapsules (e.g., encapsulated live cells together with microspheres) of the present invention, having a predefined diameter and a shell thickness, a double-emulsion approach is taken by allowing the discontinuous phase of the mixed interior core solution to coalesce and form the core of the particle and then coating the preformed microparticles with an outer shell solution. "Double-wall" particles comprising polymer cores and shells can be formed by controlling phase separation of the two sphere-forming materials. In one embodiment, a precision core-shell microparticle fabrication technique may be used as described in U.S. Pat. Nos. 8,663,511 or 8,293,271 discussed above, and incorporated by reference herein in its entirety. Briefly, in this method, for example, utilizes an apparatus which is designed having an outer nozzle operable to discharge an outer stream and an inner nozzle placed within the outer nozzle operable to discharge an inner stream, which are acoustically excited to break up into uniform core-shell droplets.

Generally, as described in more detail elsewhere herein, separate polymer, e.g., alginate, solutions (the mixed interior core solution and the outer shell solution) provided from two separate syringe pumps can be combined into a coaxial jet configuration using a coaxial nozzle. The resulting coaxial jet, with different properties, can be subsequently broken up into a train of uniform core-shell droplets by acoustic excitation at a rate of approximately 1000-4000 drops/s. Relative flow rates of the two coaxial jet streams (the inner jet stream forming the inner core and the outer jet stream forming the outer shell) can be varied to control the core diameter and shell thickness of the core-shell microcapsules, thus the overall capsule size. Once uniform core-shell droplets (e.g., encapsulated cells and microspheres as described elsewhere herein) are formed, they can be hardened by immersion into divalent cations (e.g., $Ca^{2+}$), as known in the art. In some embodiments, the cells being encapsulated should occupy less than about 5% of the microcapsule volume; and the microspheres should be a few in number, with their size smaller than the interior microcapsule size by a factor of 4.

In one embodiment, the microcapsules of the present invention may include wherein the microcapsule is formed by a process comprising a microencapsulation technique using two separate polymer solutions, one being the mixed interior core polymer solution and the other, the "shell" or outer polymer solution. The two solutions from two separate syringe pumps, for example, may be combined into a coaxial jet which is then broken up into a train of uniform core-shell droplets by acoustic excitation at a rate of approximately 1000-4000 drops/s. Relative flow rates of the two coaxial jet streams (the inner jet stream forming the inner core and the outer jet stream forming the exterior shell) can be varied to control the core diameter and shell thickness of the core-shell microcapsules, thus the overall capsule size; in the present invention, the microcapsule has dimensions of between about 300 µm and about 600 µm.

In a further embodiment, the microcapsules of the present invention may include wherein the interior core is formed by spraying a mixture comprising the second polymer, the cells and the microspheres, wherein the cells are at a concentration of between $0.1 \times 10^4$ and $10 \times 10^4$ cells/ml, the polymer is at a concentration of between 0.1% (w/v) and 10% (w/v), and the microspheres comprising a compound which improves survival of the cell, at a drug load of between 1 and 30%, in a PLGA polymer. The outer shell is formed by simultaneously spraying the first polymer solution between about 0.1% w/v and 10% w/v using two separate syringe pumps into a coaxial jet configuration using a coaxial nozzle.

In another embodiment, the microcapsules of the present invention may include wherein the microcapsule is formed by a process comprising a microencapsulation technique and the microcapsule has dimensions of between about 300 µm and about 600 µm, and wherein the microencapsulation technique is a vibrational nozzle technique. In this embodiment, the microcapsules of the present invention may include wherein the interior core is formed by spraying a mixture comprising the cell at a concentration of between $0.1 \times 10^4$ and $10 \times 10^4$ cells/ml, and the polymer, wherein the polymer comprises alginate at 0.8% to 2.0% (w/v), together with microspheres comprising exenatide at about 10% w/w load and PLGA, through a vibrational nozzle. The microcapsules of the present invention may include wherein the outer shell is formed by simultaneously spraying an alginate solution which has been filtered through a membrane through a vibrational nozzle. In some embodiments, the alginate solution has been filtered through a 1 to 0.1 micron filter, and the alginate solution is at between about 5% and 0.5% (w/v). In other embodiments, the lyoprotected microcapsule of claim 12, wherein the filter is selected from a 0.8 micron, a 0.45 micron, or a 0.22 micron filter, and the alginate solution is 1.0% (w/v), 1.2% (w/v), 1.5% (w/v), or 2.0% (w/v).

In another embodiment, the microcapsules of the present invention may include wherein the microcapsule is hardened by addition of a divalent cation such as calcium ion, or a combination thereof, by methods known in the art.

Storage and Increased Survival/Function of Encapsulated Cells

After fabrication, the microcapsules can be stored in any storage solution which comprises an appropriate media for cell proliferation or cell growth. Thus, a storage solution may comprise any media adapted for support of cell growth and proliferation as known in the art. Media may comprise nutritional additives and components that can help improve and preserve function of the cell to allow for improved activity, stability, and release of the cell. This may include buffers to stabilize pH, bulking agent, salt, tonicity adjusters, such as mannitol, sucrose, glycine, glycerol, PEG and other polyhydric alcohols, amino acids such as glycine, L-serine, alanine, proline, phenylalanine, arginine, proline, sodium chloride, and additional nutrients for improved survival and activity. In one embodiment, an appropriate storage solution is RPMI-1640 containing 10% FBS and 1% Pen/Strep. Incubation may occur at 37° C. in 5% $CO_2$.

In order to assess survival and/or function of the cells, at scheduled time points, the viability and function of the encapsulated cells may be assessed. The assay for viability and function will be dependent on the type of cells that are encapsulated, as is known in the art. Where the cells are encapsulated islet cells, the encapsulated islets can be assessed for survival and function by trypan blue exclusion and insulin secretory response during glucose stimulation, respectively, by methods known in the art. Morphology of the cells may also be determined and used to assess cell health and survival as known in the art.

In order to assess survivability and function, in one embodiment, the culture medium is refreshed every other day during a 21-day period. In one embodiment, the viability of islets immediately after isolation and after overnight incubation, and prior to encapsulation, was either 96.4±0.7 and 93.4±3.4%. The viability immediately after the encapsulation in the AL (microcapsules made by the methods disclosed herein but not containing microspheres) and AL-extMS capsules (microcapsules made by the methods disclosed herein and containing microcapsules) (Day 0) was 90.8±3.5% and 91.6±3.6%, respectively, revealing minimal stress during encapsulation. The inventors observed that there was no significant difference in the viability between the islets in the AL and the AL-extMS capsules at Day 1 post-encapsulation. The viability of the islets in the AL and AL-extMS capsules began to decrease at Day 3 and Day 5, respectively. The AL capsules exhibited a rapid reduction in islet viability from Day 5, but the AL-extMS a slow decrease over time. As a result, the viability of the islets in the AL and the AL-extMS capsules was 69.7±3.6% and 82.3±3.3%, respectively, at Day 10 and 45.1±4.9% and 71.1±4.8%, respectively, at Day 21, manifesting the beneficial effect of the latter on islet viability.

Accordingly, in one embodiment, the islet cells in the microcapsules exhibit survival of at least 50%, at least 55%, at least 60%, at least 65%, at least 70%, at least 75%, or at least 80%, at day 10 of incubation in RPMI-1640 comprising 10% FBS and 1% pen/strep at 37° C. In another embodiment, the islet cells in the microcapsules exhibit survival of at least 40%, at least 45%, at least 50%, at least 55%, at least 60%, at least 65%, or at least 70% at day 21 of incubation in RPMI-1640 comprising 10% FBS and 1% pen/strep at 37° C.

Figure 4A:
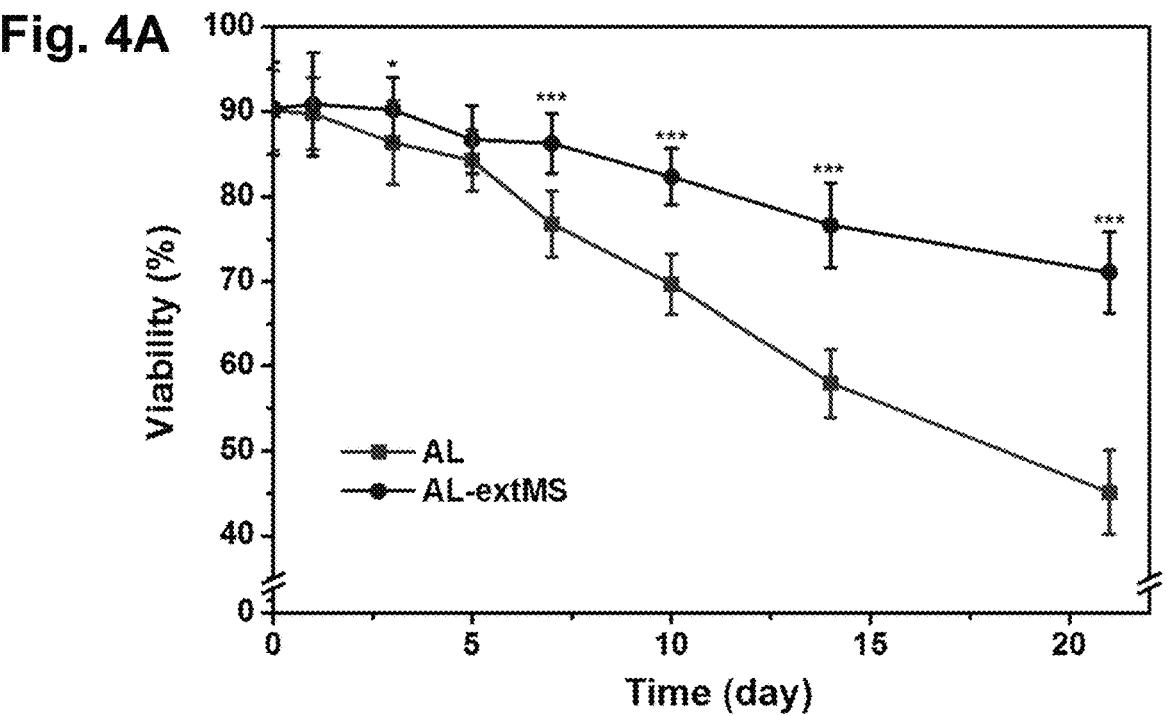
FIG. 4A-4B.
Figure 4B:
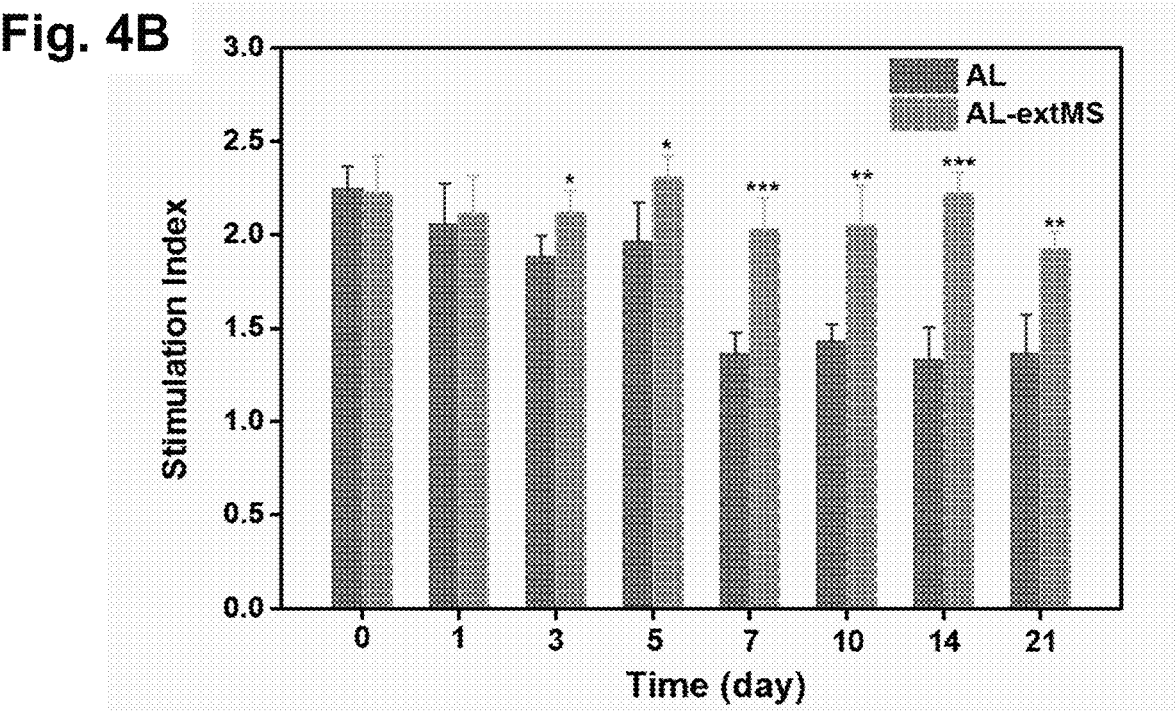
Figure 5:
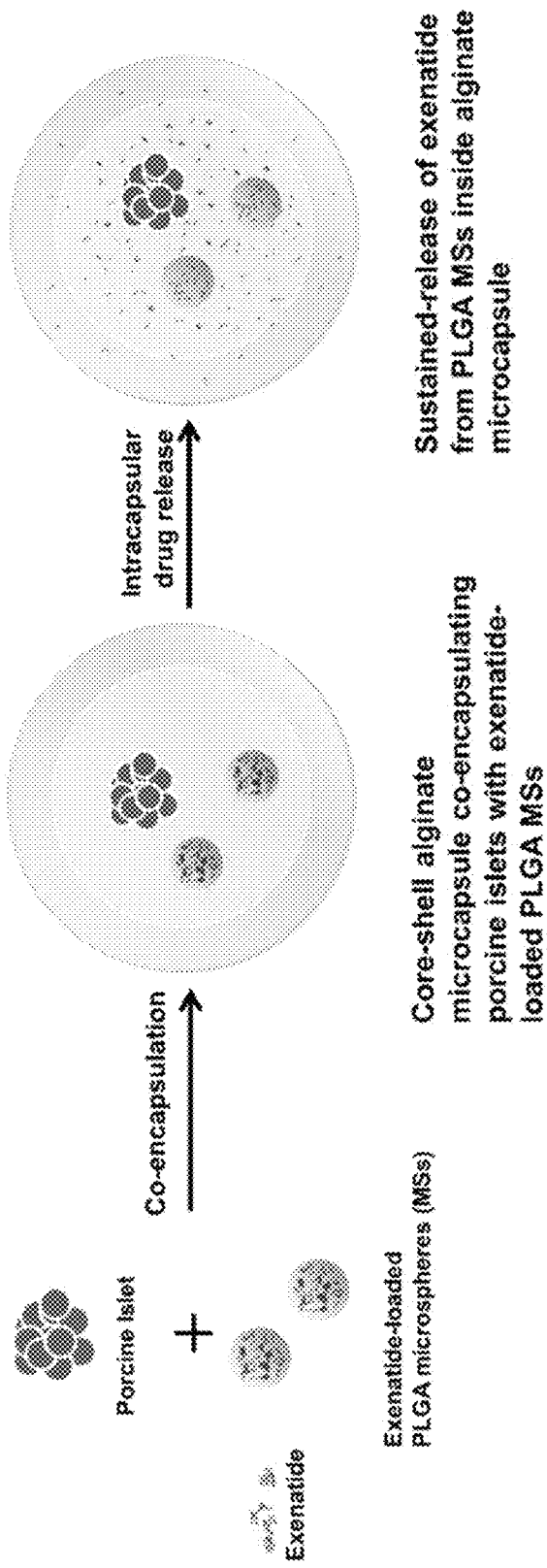
FIG. 5. Schematic of the process for making the capsules.

To assess function, for islet cells, in one embodiment and in vitro glucose-stimulated insulin secretion (GSIS) assessment was performed by methods known in the art. In that assay, encapsulated islets of 500 IEQ can be separately exposed to low (1.67 mM) or high glucose (16.7 mM) for 60 min at 37° C. in 5% $CO_2$. Insulin levels can be determined with porcine insulin ELISA assay kit and expressed as stimulation index (SI). FIG. 4B presents the stimulation index (SI) of the islets encapsulated in the AL and the AL-extMS capsules versus time, calculated as a ratio of high to low GSIS. At Day 1, no significant difference in the SIs was observed between the islets in the AL capsules and those in the AL-extMS capsules. The SI of the former began to decrease at Day 3 and decreased abruptly after Day 5, suggesting β-cell failure. The rapid reduction in the viability of the former, seen in FIG. 4A, supports this result. In contrast, the latter maintained high SIs during the entire 21-day period, consistent with their viability data in FIG. 4A. This demonstrated the positive effects of intracapsular sustained exenatide delivery on improving the survival and function of the encapsulated porcine islets.

Accordingly, in one embodiment, the islet cells in the microcapsules exhibit stimulation index of at least 1.5, at least 1.6, at least 1.7, at least 1.8, at least 1.9, at least 2.0, after 1, 3, 5, 7, 10, 14 or 21 days.

Insulin Producing System and Methods to Treat Disease

In one embodiment, the present invention includes an insulin-producing system, and/or a method of delivery of insulin to a patient in need thereof, comprising a microcapsule made by the methods disclosed herein, or comprising a microcapsule as disclosed herein.

In one embodiment, the present invention includes a method to treat diabetes, and diabetic-related conditions, comprising administering an effective amount of the microcapsule made by the methods disclosed herein, or comprising a microcapsule as disclosed herein, to the patient. Diabetic-related conditions include, but are not limited to, diabetes characterized by the presence of elevated blood glucose levels, such as hyperglycemic disorders, for example, diabetes mellitus, including both type 1 and type 2 diabetes as well as other diabetic-related disorders such as obesity, increased cholesterol, kidney-related disorders, decreased liver GK activity and the like. The above-described methods may be employed to lower insulin levels, improve glucose tolerance, increase hepatic glucose utilization, normalize blood glucose levels, increase apo A-I and HDL levels, decrease fibrinogen levels, stimulate hepatic fatty acid oxidation, reduce hepatic triglyceride accumulation and normalize glucose tolerance.

Diabetes mellitus can be subdivided into two distinct types: Type 1 diabetes and Type 2 diabetes. Type 1 diabetes is characterized by little or no circulating insulin, and it most commonly appears in childhood or early adolescence. It is caused by the destruction of the insulin-producing beta cells in the islets of Langerhans; which are scattered throughout the pancreas, an elongated gland located transversely behind the stomach. The beta cells are attacked by an autoimmune reaction initiated by some as yet unidentified environmental event. When the number of beta cells drops to a critical level (10% of normal), blood glucose levels no longer can be controlled and progression to total insulin production failure is almost inevitable.

Type 2 diabetes usually appears in middle age or later and particularly affects those who are overweight. In Type 2 diabetes, the body's cells that normally require insulin lose their sensitivity and fail to respond to insulin normally. Ultimately, the overworked beta cells die and insulin secretion fails, bringing with it a concomitant rise in blood glucose to sufficient levels that it can only be controlled by exogenous insulin injections. Another form of diabetes is called Maturity Onset Diabetes of the Young (MODY). Beta cells in patients with MODY cannot produce insulin correctly in response to glucose, which results in hyperglycemia. The patients treatment eventually leads to the requirement for insulin injections.

The currently available medical treatments for insulin-dependent diabetes are limited to insulin administration and pancreas transplantation with either whole pancreata or pancreatic segments. Insulin therapy is by far more prevalent than pancreas transplantation. Insulin administration is conventionally either by a few blood glucose measurements and subcutaneous injections, intensively by multiple blood glucose measurements and through multiple subcutaneous injections of insulin, or by continuous subcutaneous injections of insulin with a pump. However, controlling blood sugar is not simple. Despite rigorous attention to maintaining a healthy diet, exercise regimen, and always injecting the proper amount of insulin, many other factors can adversely affect a person's blood-sugar including stress, hormonal changes, periods of growth, illness, infection and fatigue. People with Type 1 diabetes must constantly be prepared for life threatening hypoglycemic (low blood sugar) and hyperglycemic (high blood sugar) reactions. Insulin-dependent diabetes is a life threatening disease, which requires never-ending vigilance.

Administration of the microcapsules of the present invention may include the step of implanting the composition into an implantation site in a patient in need of treatment for diabetes and diabetic-related conditions. In a preferred embodiment, the implantation site is subcutaneous, intramuscular, intraorgan, arterial/venous vascularity of an organ, cerebro-spinal fluid, or lymphatic fluid. More preferably, the implantation site is subcutaneous. In a most preferred embodiment, the method includes implanting the microcapsules of the invention in a subcutaneous implantation site. Appropriate methodology for implantation of microcapsules comprising a cell, such as an islet cell, are known in the art and can be determined by a practitioner of ordinary skill in the art, such as a physician.

In a preferred embodiment, the method of implanting the composition into an implantation site in patient in need of treatment for a disease or disorder also includes the step of administering an immunosuppressant or anti-inflammatory agent. Preferably, the immunosuppressant or anti-inflammatory agent is administered for less than 6 months. More preferably, the immunosuppressant or anti-inflammatory agent is administered for less than 1 month.

The term "therapeutically effective amount" shall mean that amount of protein or compound that will elicit the biological or medical response of a tissue, system or animal (mammal) that is being sought by a researcher or clinician.

The terms "subject" or "patient" are used interchangeably herein and include, but are not limited to, humans, dogs, cats, horses and cows. The preferred patients are humans.

The term "treat" or "treatment" encompasses the complete range of therapeutically positive effects associated with pharmaceutical medication including reduction of, alleviation of and relief from the symptoms or illness, which affect the organism. When treating diabetes, treatment includes the administration of a compound and/or the administration of a protein product by gene therapy to lower insulin levels, improve glucose tolerance and normalize the blood glucose level in the patient suffering from the hyperglycemic disorder. Normalize means to reduce the blood glucose level to an acceptable range, which means within 10, 8 or 5% of the normal average blood glucose level for the subject. Treating and treatment is also defined to alleviate a disease or disorder in a subject, such as a human, by the dosage of encapsulated cells or tissue to the subject in need of treatment via subcutaneous injection or implant, or directly into organs via either direct injection into the substance of the organ or injection through the vascular system of those organs and includes: (a) prophylactic treatment in a subject, particularly when the subject is found to be predisposed to having the disease or disorder but not yet diagnosed as having it; (b) inhibiting the disease or disorder; and/or (c) eliminating, in whole or in part, the disease or disorder; and/or (d) improving the subject's health and well-being.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

Example 1

Sodium alginate, Tween 20, sodium citrate, $CaCl_2$, glycerol, trehalose, and maltodextrin were purchased from Sigma-Aldrich (Milwaukee, Wis., USA). Luria-Bertani (LB) broth and agar were purchased from Fisher Scientific (Waltham, Mass. USA) and BD (Franklin Lakes, N.J., USA), respectively. All chemicals were used without further purification.

Characterization of Exenatide-Loaded PLGA MSs and In Vitro Release

PLGA has been widely used as a medical-grade biodegradable polymer in surgical sutures, bone plates, orthopedic implants and drug delivery system (Ma, 2014; Ramazani et al., 2016; Shive and Anderson, 1997). We fabricated exenatide-loaded MSs employing PLGA as a carrier material. Table 1 summarizes the drug loading, loading efficiency and size of the exenatide-loaded PLGA MSs. The loading efficiency was ~85% for a 5% theoretical loading, which decreased to ~80% as the loading increased to 10%, while the size increased with the exenatide loading. FIG. 1 shows the optical and SEM images of the PLGA MSs loaded with or without exenatide, exhibiting their dense and smooth surface morphology and size uniformity with small coefficients of variation (<2.2%).

TABLE 1

Drug loading and loading efficiency of exenatide-loaded PLGA MSs

| Theoretical loading [%, w/w] | Drug loading[a] [%, w/w] | Loading efficiency[b] [%] | Microsphere size Mean diameter ± SD [μm] |
|---|---|---|---|
| 0 | 0 | 0 | 40.92 ± 0.83 |
| 5 | 4.20 ± 0.25 | 84.06 ± 5.09 | 45.41 ± 0.97 |
| 10 | 7.91 ± 0.55 | 79.08 ± 5.50 | 51.67 ± 1.10 |

[a]Drug loading (%, w/w) = $\frac{\text{Weight of exenatide in microspheres}}{\text{Weight of exenatide} - \text{loaded microspheres}} \times 100$

[b]Loading efficiency (%) = $\frac{\text{Drug loading}}{\text{Theoretical loading}} \times 100$ FIG. 2 shows the drug release profiles of the PLGA MSs with 5 and 10% (w/w) theoretical loadings of exenatide. The exenatide-loaded MSs exhibited a low initial release, i.e., 11-13%, within 24 h.

Example 2

Morphology, Viability and Function of Encapsulated Islets

Figure 3:
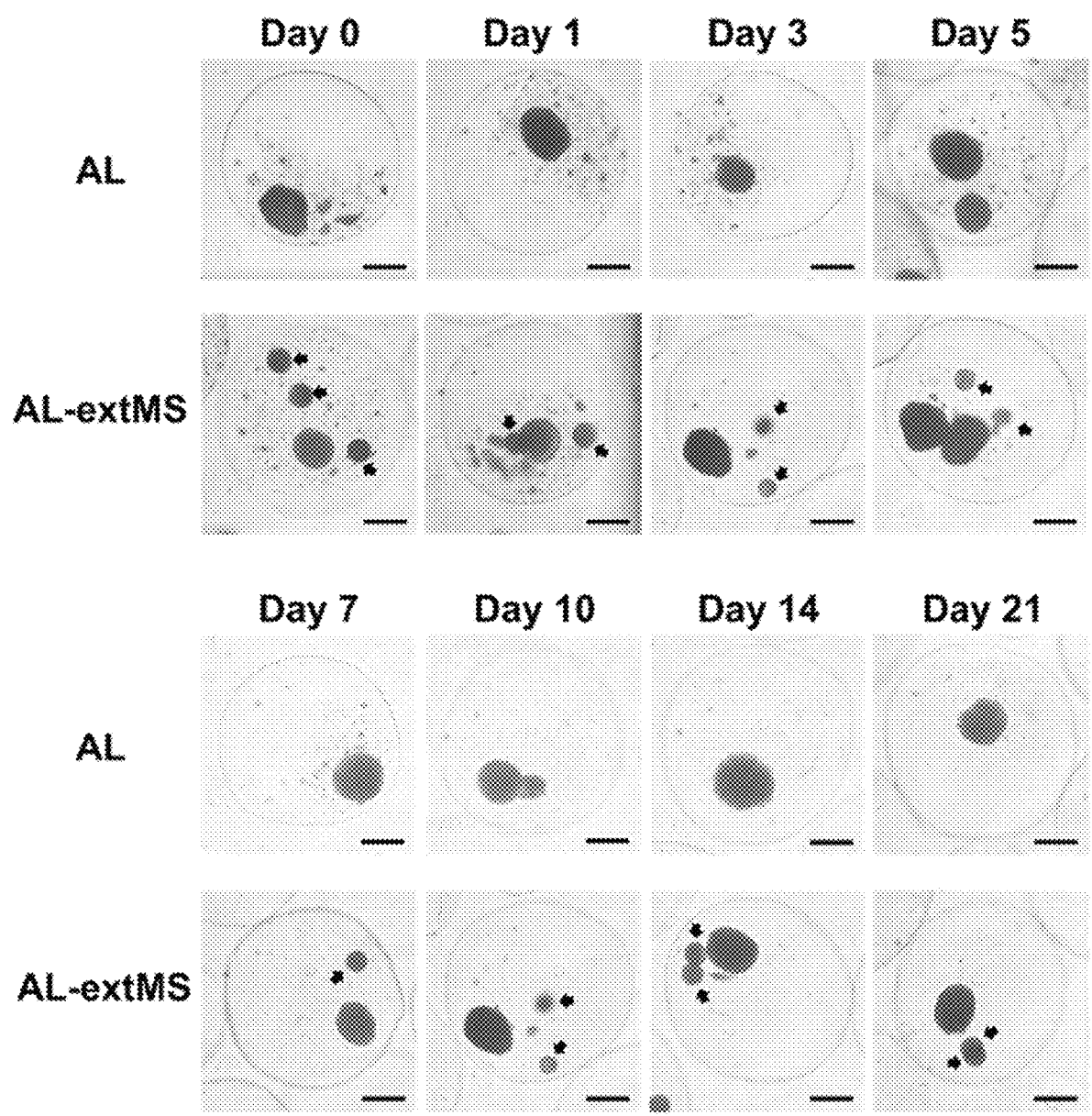
FIG. 3. Optical images of the porcine islets encapsulated in alginate (AL) microcapsules and AL microcapsules co-encapsulating 10% (w/w) exenatide-loaded MSs (AL-extMS) against time. Arrows indicate exenatide-loaded MSs. Scale bar=100 μm.

Previously, we reported the fabrication of bacterial cell-encapsulating alginate microcapsules by the PPF method, confining the cells in the capsule core (Kim et al., 2012). This method was employed to encapsulate porcine islets in alginate (AL) microcapsules with no islet protrusion. To investigate the effect of sustained delivery of exenatide on the encapsulated islets for 21 days, we selected 10% (w/w) exenatide-loaded MSs (extMS) and encapsulated them with porcine islets in the AL microcapsules. FIG. 3 shows the optical images of the islets encapsulated in the AL capsules and the ext-MS co-encapsulating AL (AL-extMS) capsules. The capsules were spherical with a mean diameter of 411.0±11.6 μm, exhibiting no protrusion of islets or spheres. No notable physical difference was observed between the islets encapsulated in the AL and those in the AL-extMS capsules until Day 5; however, the islet morphology became distinctive for each capsule type afterwards. In the AL capsules from Day 7 to 21, individual cells began to protrude from the islet surface, indicating decreased or decreasing health (Carter et al., 2009). The islets in the AL-extMS capsules maintained their morphological integrity until Day 21. FIG. 4A shows the viability of the islets encapsulated in the AL and the AL-extMS capsules for 21 days. The viability of islets immediately after isolation and after overnight was 96.4±0.7 and 93.4±3.4%, respectively, and that immediately after the encapsulation in the AL and AL-extMS capsules (Day 0) 90.8±3.5% and 91.6±3.6%, respectively, revealing minimal stress during encapsulation. There was no significant difference in the viability between the islets in the AL and the AL-extMS capsules at Day 1 post-encapsulation. The viability of the islets in the AL and AL-extMS capsules began to decrease at Day 3 and Day 5, respectively. The AL capsules exhibited a rapid reduction in islet viability from Day 5, but the AL-extMS a slow decrease over time. As a result, the viability of the islets in the AL and the AL-extMS capsules was 69.7±3.6% and 82.3±3.3%, respectively, at Day 10 and 45.1±4.9% and 71.1±4.8%, respectively, at Day 21, manifesting the beneficial effect of the latter on islet viability. The effect of the AL-extMS capsules on islet function was assessed by GSIS assay. FIG. 4B presents the stimulation index (SI) of the islets encapsulated in the AL and the AL-extMS capsules versus time, calculated as a ratio of high to low GSIS. At Day 1, no significant difference in the SIs was observed between the islets in the AL capsules and those in the AL-extMS capsules. The SI of the former began to decrease at Day 3 and decreased abruptly after Day 5, suggesting β-cell failure (Prentki and Nolan, 2006). The rapid reduction in the viability of the former, seen in FIG. 4A supports this. In contrast, the latter maintained high SIs during the entire 21-day period, consistent with their viability data in FIG. 4A. This demonstrated the positive effects of intracapsular sustained exenatide delivery on improving the survival and function of the encapsulated porcine islets.

Example 3

Poly(lactic-co-glycolic acid) (PLGA) (50:50 lactic acid/glycolic acid; [i.v.]=0.58 dL/g in hexafluoroisopropanol) were obtained from Absorbable Polymers (Birmingham, Ala., USA). Poly(vinyl alcohol) (PVA) (80% hydrolyzed; MW~6,000) were purchased from Polysciences, Inc. Exenatide acetate were obtained from Bachem Americas, Inc. (Torrance, Calif., USA). Protanal® SF 120 alginate (from *Laminaria hyperborea*; Mw 237K, FG 0.694) was obtained from FMC BioPolymer (Drammen, Norway). Alginate solutions were filtered through cellulose acetate membranes with pore sizes of 0.8, 0.45, and 0.22 μm, consecutively. Tween 20, CaCl$_2$ and BaCl$_2$ were purchased from Sigma-Aldrich (St. Louis, Mo., USA). All chemicals were used without further purification.

Fabrication and Characterization of Exenatide-Loaded PLGA MSs

Exenatide-loaded PLGA MSs were fabricated by the PPF method as previously described (Berkland et al., 2001; Berkland et al., 2002; Cheng et al., 2011; Liu et al., 2010). Briefly, a desired amount of exenatide was dissolved in a 1% (w/v) PVA solution, added to a 5% (w/v) PLGA solution in dichloromethane (DCM) and emulsified by sonication for 30 s. The emulsion and 1% (w/v) PVA solution were fed into the coaxial nozzle and broken up into uniform droplets by acoustic excitation. The resulting droplets were collected in a bath containing a 1% (w/v) PVA solution and hardened. Thus-obtained MSs were washed three times with deionized water, freeze-dried (Labconco benchtop model, Kansas, Mo., USA), and stored in a sealed tube at −20° C. The morphology of the PLGA MSs with 0, 5, and 10% (w/w) loadings was observed by optical (Olympus BX51, Olympus America Inc., USA) and scanning electron microscopy (Hitachi S4800 High Resolution SEM, Japan). The drug loading and loading efficiency were determined by the bicinchoninic acid (BCA) assay (Thermo Scientific, Waltham, Mass., USA), after dissolving the exenatide-loaded MSs in DCM and acetone (Meinel et al., 2001).

In vitro exenatide release from the PLGA MSs was measured by suspending 20 mg MSs in 1 ml of assay medium (PBS with 2 mM sodium dodecyl sulfate (SDS)) at 37° C. under continuous agitation at 100 rpm (Geng et al., 2008). At designed time intervals, the suspension was centrifuged at 6000 rpm for 5 min, the supernatant was transferred to a 1.5 ml tube, and an equal volume of fresh medium was added to the precipitate for the next assay. The transferred medium was centrifuged at 12,000 rpm for 10 min to quantify the released exenatide by the BCA assay (Thermo Scientific, Waltham, Mass., USA).

Porcine Islet Isolation

Islet isolation was performed using modified Ricordi method (Ricordi et al., 1986) from the pancreas of 4-6 month old hybrid pigs, procured from the Meat Science Laboratory at the University of Illinois. Briefly, the pancreas was perfused and digested with Hanks' balanced salt solution (HBSS) with 10% fetal bovine serum (FBS) containing collagenase (from *Clostridium histolyticum*, Sigma, St. Louis, Mo., USA), followed by filtration, centrifugation and discontinuous Ficoll® 400 (Sigma, St. Louis, Mo., USA) density gradient centrifugation. The isolated islets were resuspended in RPMI-1640 containing 10% FBS and 1% Pen/Strep for incubation at 37° C. in 5% $CO_2$. Isolation outcome was evaluated by converting islets to islet equivalents (IEQ) with an average diameter of 150 µm (3,918 IEQ/g) and islet viability by trypan blue exclusion (Brandhorst et al., 1999; Shimoda et al., 2012).

Islet Encapsulation

The PPF method was employed to encapsulate islets (Kim et al., 2012). Briefly, a 2.0% (w/v) Protanal® SF 120 sodium alginate solution was prepared in $dH_2O$ (pH 7.2-7.4) as a shell solution. Isolated porcine islets were centrifuged at 3,000 rpm for 5 min at room temperature. After decanting the medium, the islets were resuspended in a 1.5% alginate solution (10,000 islets/ml) to be used as a core solution. The alginate solutions were fed into the coaxial nozzle to produce a jet, which was broken up into core/shell droplets and collected in a gelling solution containing 50 mM $CaCl_2$, 1 mM $BaCl_2$ and 0.05% (w/v) Tween 20 in $dH_2O$ (pH 7.2-7.4). Alginate capsules co-encapsulating islets and exenatide-loaded PLGA MSs were prepared by adding MSs (1.5 mg/ml) to the core solution. The resulting capsules were washed with PBS and transferred to RPMI-1640 containing 10% FBS and 1% Pen/Strep for incubation at 37° C. in 5% $CO_2$. Optical images were used to determine the size and size distribution of the capsules, analyzing>200 capsules.

In Vitro Evaluation of Encapsulated Islets

At scheduled time points, the viability and function of encapsulated islets were assessed by trypan blue exclusion and insulin secretory response during glucose stimulation, respectively (Brandhorst et al., 1999; Ricordi et al., 1990; Shimoda et al., 2012). For in vitro GSIS assessment, encapsulated islets of 500 IEQ were separately exposed to low (1.67 mM) or high glucose (16.7 mM) for 60 min at 37° C. in 5% $CO_2$. Insulin levels were determined with porcine insulin ELISA assay kit (Mercodia, Uppsala, Sweden) and expressed as stimulation index (SI), calculated as the ratio of high to low GSIS. The morphology of encapsulated islets was observed using an optical microscope (Olympus BX51, Olympus America Inc., USA). The culture medium was refreshed every other day during the 21-day period.

Statistical Analysis

All data are expressed as mean±standard deviation (SD) for four replicates. Data comparisons were performed by one-way ANOVA with Tukey's post hoc test for multiple comparisons. Differences with $p<0.05$ were considered statistically significant.

REFERENCES

Berkland, C., Kim, K., Pack, D. W., 2001. Fabrication of PLG microspheres with precisely controlled and monodisperse size distributions. Journal of controlled release 73, 59-74.

Berkland, C., King, M., Cox, A., Kim, K., Pack, D. W., 2002. Precise control of PLG microsphere size provides enhanced control of drug release rate. Journal of controlled release 82, 137-147.

Brandhorst, H., Brandhorst, D., Hering, B. J., Bretzel, R. G., 1999. Significant progress in porcine islet mass isolation utilizing liberase HI for enzymatic low-temperature pancreas digestion. Transplantation 68, 355-361.

Carter, J. D., Dula, S. B., Corbin, K. L., Wu, R., Nunemaker, C. S., 2009. A practical guide to rodent islet isolation and assessment. Biological procedures online 11, 3-31.

Cheng, F., Choy, Y. B., Choi, H., Kim, K. K., 2011. Modeling of small-molecule release from crosslinked hydrogel microspheres: effect of crosslinking and enzymatic degradation of hydrogel matrix. International journal of pharmaceutics 403, 90-95.

de Groot, M., Schuurs, T. A., van Schilfgaarde, R., 2004. Causes of limited survival of microencapsulated pancreatic islet grafts. The journal of surgical research 121, 141-150.

Gaba, R. C., Garcia-Roca, R., Oberholzer, J., 2012. Pancreatic islet cell transplantation: an update for interventional radiologists. Journal of vascular and interventional radiology: JVIR 23, 583-594; quiz 594.

Geng, Y., Yuan, W., Wu, F., Chen, J., He, M., Jin, T., 2008. Formulating erythropoietin-loaded sustained-release PLGA microspheres without protein aggregation. Journal of controlled release 130, 259-265.

Jeong, J. H., Yook, S., Jung, Y., Im, B. H., Lee, M., Ahn, C. H., Lee, D. Y., Byun, Y., 2012. Functional enhancement of beta cells in transplanted pancreatic islets by secretion signal peptide-linked exendin-4 gene transduction. Journal of controlled release 159, 368-375.

Kim, I. Y., Pusey, P. L., Zhao, Y., Korban, S. S., Choi, H., Kim, K. K., 2012. Controlled release of *Pantoea agglomerans* E325 for biocontrol of fire blight disease of apple. Journal of controlled release 161, 109-115.

Lim, F., Sun, A. M., 1980. Microencapsulated islets as bioartificial endocrine pancreas. Science 210, 908-910.

Liu, B., Dong, Q., Wang, M., Shi, L., Wu, Y., Yu, X., Shi, Y., Shan, Y., Jiang, C., Zhang, X., Gu, T., Chen, Y., Kong, W., 2010. Preparation, characterization, and pharmacodynamics of exenatide-loaded poly(DL-lactic-co-glycolic acid) microspheres. Chemical & pharmaceutical bulletin 58, 1474-1479.

Ma, G., 2014. Microencapsulation of protein drugs for drug delivery: strategy, preparation, and applications. Journal of controlled release 193, 324-340.

Meinel, L., Illi, O. E., Zapf, J., Malfanti, M., Peter Merkle, H., Gander, B., 2001. Stabilizing insulin-like growth factor-I in poly(D,L-lactide-co-glycolide) microspheres. Journal of controlled release 70, 193-202.

Mineo, D., Pileggi, A., Alejandro, R., Ricordi, C., 2009. Point: steady progress and current challenges in clinical islet transplantation. Diabetes care 32, 1563-1569.

Padmasekar, M., Lingwal, N., Samikannu, B., Chen, C., Sauer, H., Linn, T., 2013. Exendin-4 protects hypoxic islets from oxidative stress and improves islet transplantation outcome. Endocrinology 154, 1424-1433.

Pileggi, A., Ricordi, C., Alessiani, M., Inverardi, L., 2001. Factors influencing Islet of Langerhans graft function and monitoring. Clinica chimica acta; international journal of clinical chemistry 310, 3-16.

Potter, K. J., Abedini, A., Marek, P., Klimek, A. M., Butterworth, S., Driscoll, M., Baker, R., Nilsson, M. R., Warnock, G. L., Oberholzer, J., Bertera, S., Trucco, M., Korbutt, G. S., Fraser, P. E., Raleigh, D. P., Verchere, C. B., 2010. Islet amyloid deposition limits the viability of human islet grafts but not porcine islet grafts. Proceedings of the National Academy of Sciences of the United States of America 107, 4305-4310.

Prentki, M., Nolan, C. J., 2006. Islet beta cell failure in type 2 diabetes. The Journal of clinical investigation 116, 1802-1812.

Qi, F., Wu, J., Fan, Q., He, F., Tian, G., Yang, T., Ma, G., Su, Z., 2013. Preparation of uniform-sized exenatide-loaded PLGA microspheres as long-effective release system with high encapsulation efficiency and bio-stability. Colloids and surfaces. B, Biointerfaces 112, 492-498.

Qi, M., 2014. Transplantation of Encapsulated Pancreatic Islets as a Treatment for Patients with Type 1 Diabetes Mellitus. Advances in medicine 2014, 429710.

Ramazani, F., Chen, W., van Nostrum, C. F., Storm, G., Kiessling, F., Lammers, T., Hennink, W. E., Kok, R. J., 2016. Strategies for encapsulation of small hydrophilic and amphiphilic drugs in PLGA microspheres: State-of-the-art and challenges. International journal of pharmaceutics 499, 358-367.

Ricordi, C., Finke, E. H., Lacy, P. E., 1986. A method for the mass isolation of islets from the adult pig pancreas. Diabetes 35, 649-653.

Ricordi, C., Gray, D. W., Hering, B. J., Kaufman, D. B., Warnock, G. L., Kneteman, N. M., Lake, S. P., London, N. J., Socci, C., Alejandro, R., et al., 1990. Islet isolation assessment in man and large animals. Acta diabetologica latina 27, 185-195.

Sakata, N., Sumi, S., Yoshimatsu, G., Goto, M., Egawa, S., Unno, M., 2012. Encapsulated islets transplantation: Past, present and future. World journal of gastrointestinal pathophysiology 3, 19-26.

Sato, Y., Endo, H., Okuyama, H., Takeda, T., Iwahashi, H., Imagawa, A., Yamagata, K., Shimomura, I., Inoue, M., 2011. Cellular hypoxia of pancreatic beta-cells due to high levels of oxygen consumption for insulin secretion in vitro. The journal of biological chemistry 286, 12524-12532.

Shimoda, M., Noguchi, H., Fujita, Y., Takita, M., Ikemoto, T., Chujo, D., Naziruddin, B., Levy, M. F., Kobayashi, N., Grayburn, P. A., Matsumoto, S., 2012. Improvement of porcine islet isolation by inhibition of trypsin activity during pancreas preservation and digestion using alpha1-antitrypsin. Cell transplantation 21, 465-471.

Shive, M. S., Anderson, J. M., 1997. Biodegradation and biocompatibility of PLA and PLGA microspheres. Advanced drug delivery reviews 28, 5-24.

Wynyard, S., Nathu, D., Garkavenko, O., Denner, J., Elliott, R., 2014. Microbiological safety of the first clinical pig islet xenotransplantation trial in New Zealand. Xenotransplantation 21, 309-323.

Yang, H. K., Yoon, K. H., 2015. Current status of encapsulated islet transplantation. Journal of diabetes and its complications 29, 737-743.

Zhu, C., Huang, Y., Zhang, X., Mei, L., Pan, X., Li, G., Wu, C., 2015. Comparative studies on exenatide-loaded poly (D,L-lactic-co-glycolic acid) microparticles prepared by a novel ultra-fine particle processing system and spray drying. Colloids and surfaces. B, Biointerfaces 132, 103-110.

Zhu, H. T., Wang, W. L., Yu, L., Wang, B., 2014. Pig-islet xenotransplantation: recent progress and current perspectives. Frontiers in surgery 1, 7.

The invention claimed is:

1. A microcapsule for improved survival and/or function of encapsulated cells, comprising:
   an outer shell comprising a;
   an interior core having a diameter, the interior core comprising:
     at least one live cell;
     alginate; and
     intracapsular microspheres, wherein the microspheres are prepared via a monodispersed emulsion comprising an aqueous polyvinyl alcohol solution, a beneficial compound mixture configured to improve survival of the at least one cell, and a PLGA solution in dichloromethane, the aqueous polyvinyl alcohol is between 0.1 and 10%, the PLGA solution is between 2-10% load; wherein all of the intracapsular microspheres have a coefficient of variation of not greater than 2.2% with respect to diameter;
   wherein each of the intracapsular microspheres has a diameter that is at least about 4 times smaller than the diameter of the interior core;
   wherein the concentration of the alginate in the outer shell is higher than the concentration of the alginate in the interior core; and
   wherein the at least one live cell and each microsphere are completely contained within the interior core such that they do not protrude from the outer shell; and
   wherein the interior core is formed by spraying an interior core mixture comprising the live cell at between $1 \times 10^3$ and $1 \times 10^5$ cells/ml, alginate at 0.8% to 2.0% (w/v), and the microspheres at between 0.5 and 15 mo/ml through a coaxial vibrational nozzle, and wherein the outer shell is formed by simultaneously spraying the interior core solution with a first polymer solution comprising an alginate solution through the coaxial vibrational nozzle.

2. The microcapsule of claim 1, wherein the live cell is a porcine pancreatic islet cell.

3. The microcapsule of claim 2, wherein the beneficial compound comprises one or more of a glucagon-like peptide-1 (GLP-1) receptor agonist, an anti-inflammatory drug, a pro-angiogenic drug, a chelating agent, and a corticosteroid.

4. The microcapsule of claim 3, wherein the GLP-1 receptor agonist is selected from the group consisting of exenatide, exendin-4, truncated exendin-4, esterified exendin-4, N-alkyl exendin-4, PEG-modified exendin-4, liraglutide, lixisenatide, dulaglutide, taspoglutide, and semaglutide.

5. The microcapsule of claim 2, wherein the microspheres have a mean diameter of between 10 μm to about 100 μm.

6. The microcapsule of claim 1, the outer shell having a diameter at least 8 times larger than the diameter of each of the microspheres.

* * * * *

UNITED STATES PATENT AND TRADEMARK OFFICE
CERTIFICATE OF CORRECTION

PATENT NO. : 11,471,419 B2
APPLICATION NO. : 15/721045
DATED : October 18, 2022
INVENTOR(S) : Kim et al.

It is certified that error appears in the above-identified patent and that said Letters Patent is hereby corrected as shown below:

In the Claims

• In Claim 1 (Column 28, Line 13), please replace "an outer shell comprising a;" with --an outer shell comprising a alginate;--

Signed and Sealed this
Thirty-first Day of January, 2023

Katherine Kelly Vidal
*Director of the United States Patent and Trademark Office*